United States Patent
Nirogi et al.

(10) Patent No.: US 11,234,979 B2
(45) Date of Patent: Feb. 1, 2022

(54) HETEROARYL COMPOUNDS AS MUSCARINIC M1 RECEPTOR POSITIVE ALLOSTERIC MODULATORS

(71) Applicant: SUVEN LIFE SCIENCES LIMITED, Hyderabad-Telangana (IN)

(72) Inventors: Ramakrishna Nirogi, Hyderabad (IN); Abdul Rasheed Mohammed, Hyderabad (IN); Anil Karbhari Shinde, Hyderabad (IN); Srinivas Ravella, Hyderabad (IN); Vanaja Middekadi, Hyderabad (IN); Vinod Kumar Goyal, Hyderabad (IN); Pradeep Jayarajan, Hyderabad (IN); Saivishal Daripelli, Hyderabad (IN); Venkateswarlu Jasti, Hyderabad (IN)

(73) Assignee: Suven Life Sciences Limited, Hyderabad (IN)

( * ) Notice: Subject to any disclaimer, the term of this patent is extended or adjusted under 35 U.S.C. 154(b) by 0 days.

(21) Appl. No.: 16/753,183

(22) PCT Filed: Oct. 17, 2018

(86) PCT No.: PCT/IB2018/058047
§ 371 (c)(1),
(2) Date: Apr. 2, 2020

(87) PCT Pub. No.: WO2019/077517
PCT Pub. Date: Apr. 25, 2019

(65) Prior Publication Data
US 2020/0237761 A1    Jul. 30, 2020

(30) Foreign Application Priority Data

Oct. 18, 2017   (IN) .............. 201741037090

(51) Int. Cl.
| | | |
|---|---|---|
| *A61K 31/5025* | (2006.01) | |
| *A61P 25/28* | (2006.01) | |
| *A61K 31/13* | (2006.01) | |
| *A61K 31/27* | (2006.01) | |
| *A61K 31/437* | (2006.01) | |
| *A61K 31/445* | (2006.01) | |
| *A61K 31/473* | (2006.01) | |
| *A61K 31/55* | (2006.01) | |
| *C07D 471/04* | (2006.01) | |
| *C07D 487/04* | (2006.01) | |

(52) U.S. Cl.
CPC .......... *A61K 31/5025* (2013.01); *A61K 31/13* (2013.01); *A61K 31/27* (2013.01); *A61K 31/437* (2013.01); *A61K 31/445* (2013.01); *A61K 31/473* (2013.01); *A61K 31/55* (2013.01); *A61P 25/28* (2018.01); *C07D 471/04* (2013.01); *C07D 487/04* (2013.01)

(58) Field of Classification Search
None
See application file for complete search history.

(56) References Cited

U.S. PATENT DOCUMENTS

2016/0194321 A1    7/2016  Balllard et al.

FOREIGN PATENT DOCUMENTS

| EP | 3052496 B1 | 8/2016 |
|---|---|---|
| WO | 2011/062853 | 5/2011 |
| WO | 2015/044072 A1 | 4/2015 |
| WO | 2016/172547 | 10/2016 |
| WO | 2016/198937 | 12/2016 |
| WO | 2017/042643 | 3/2017 |

OTHER PUBLICATIONS

European Patent Office, International Search Report, PCT/IB2018/058047, Feb. 2, 2019, Rijswijk, Netherlands.
European Patent Office, Written Opinion of the International Searching Authority, PCT/IB2018/058047, Feb. 2, 2019, Berlin, Germany.
Xue, Yu et al; Synthesis and biological activities of indolizine derivatives as alpha-7 nAChR agonists, European Journal of Medicinal Chemistry, Mar. 8, 2016, vol. 115, pp. 94-108.

*Primary Examiner* — Brian J Davis
(74) *Attorney, Agent, or Firm* — IpHorgan Ltd.

(57) ABSTRACT

The present invention relates to compounds of formula (I), or their isotopic forms, stereoisomers, tautomers or pharmaceutically acceptable salt (s) thereof as muscarinic M1 receptor positive allosteric modulators (M1 PAMs). The present invention describes the preparation, pharmaceutical composition and the use of compound formula (I)

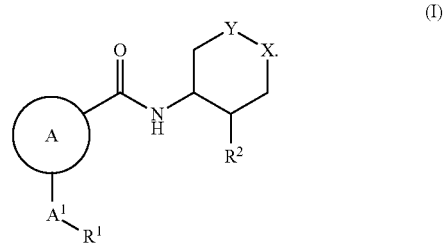

18 Claims, 1 Drawing Sheet

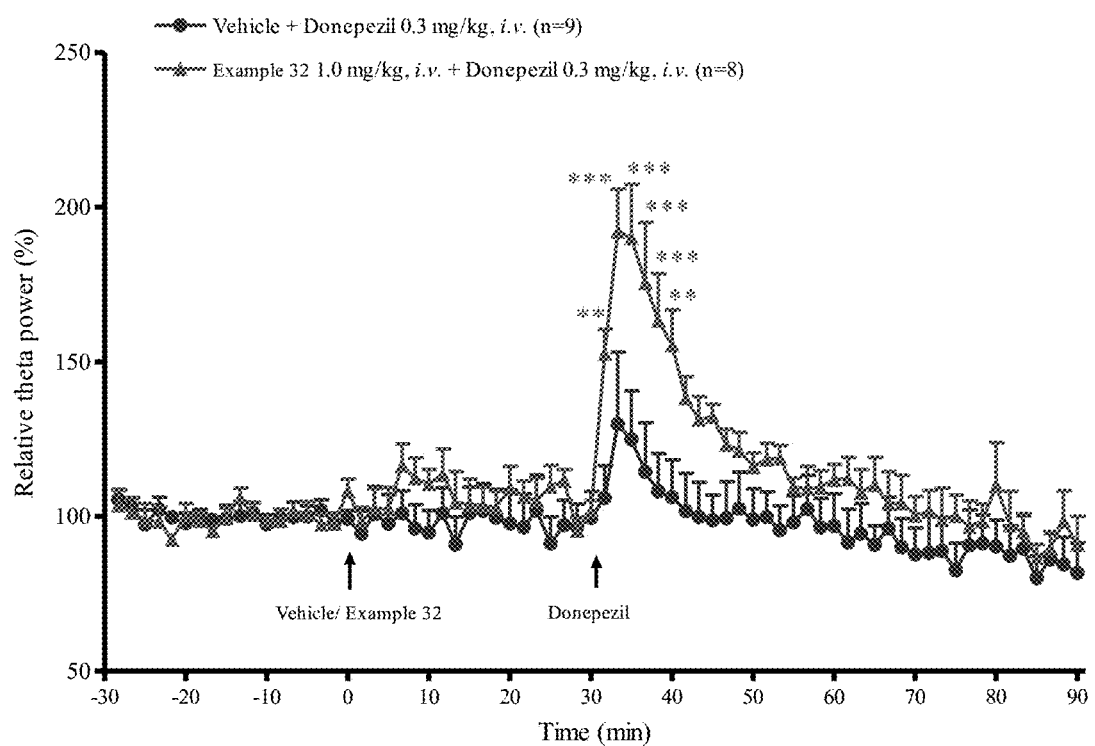

HETEROARYL COMPOUNDS AS MUSCARINIC M1 RECEPTOR POSITIVE ALLOSTERIC MODULATORS

CROSS REFERENCE TO RELATED APPLICATIONS

This application is a national stage completion application of PCT Application No. PCT/IB2018/058047, filed Oct. 17, 2018, and claims priority from India Application No. 201741037090, filed Oct. 18, 2017. Each of these applications is incorporated by reference herein in its entirety.

FIELD OF INVENTION

The present invention relates to compounds of formula (I), or their isotopic forms, stereoisomers, or pharmaceutically acceptable salts as muscarinic M1 receptor positive allosteric modulators (M1 PAMs). The present invention also describes method of making such compounds, pharmaceutical compositions comprising such compounds and their use.

BACKGROUND OF THE INVENTION

Muscarinic acetylcholine receptors (mAChRs) which belong to the class A family of G protein-coupled receptors (GPCRs), are widely expressed throughout the body. Five subtypes termed M1 through M5 that respond to the endogenous neurotransmitter acetylcholine (ACh) has been identified till date. They play key role in regulating the activity of many important functions of the central and peripheral nervous system including cognitive function. M1, M3 and M5 couple to Gq, whereas M2 and M4 couple via Gi/o to downstream signaling pathways and associated effector systems (*Critical Reviews in Neurobiology*, 1996, 10, 69-99; *Pharmacology & Therapeutics*, 2008, 117, 232-243). M2 and M3 are highly expressed in the periphery and are known to be involved in gastrointestinal (GI) motility and parasympathetic responses such as salivation (*Life Sciences*, 1993, 52, 441-448). The M1 muscarinic receptor is predominantly expressed in the brain regions such as cortex, hippocampus and amygdala which involved in cognition, and therefore selective activation of the M1 receptor would be expected to boost cognitive performance (*Annals of Neurology*, 2003, 54, 144-146).

Xanomeline, a muscarinic acetylcholine receptor agonist with reasonable selectivity for the M1 and M4 subtypes, produced significant effects on cognition in a clinical Alzheimer's disease (AD) trial (*Alzheimer Disease and Associated Disorders*, 1998, 12(4), 304-312) although gastrointestinal side effects led to a high dropout rate in clinical trials. There is a high degree of conservation between muscarinic receptor subtypes at their orthosteric acetylcholine ligand binding sites which makes it difficult to identify a M1 selective agonist.

To circumvent this issue of selectivity and safety, an alternative approach consists of developing M1 PAMs that act at the less conserved allosteric binding site. Merck reported the development of M1 PAM, PQCA (1-{[4-cyano-4-(pyridine-2-yl) piperidin-1-yl] methyl}-4-oxo-4H-quinolizine-3-carboxylic acid). This compound is highly selective for M1 over the other muscarinic receptor subtypes and found to be efficacious in several preclinical models of cognition (*Psychopharmacology*, 2013, 225(1), 21-30) with no gastrointestinal side effects at doses equal to or less than a fivefold margin from the minimum effective dose required to improve cognition. In preclinical studies it was demonstrated that M1 activation increases neurotransmitter acetylcholine concentration in brain. Moreover, the M1 activation has potential as disease-modifying therapy for AD by both shifting the APP processing towards the non-amyloidogenic α-secretase pathway and by decreasing the tau hyper-phosphorylation. Positive allosteric modulators at M1 receptor have demonstrated to increase the generation of sAPPα in-vitro (*The Journal of Neuroscience*, 2009, 29, 14271-14286). Therefore, M1 PAMs provide an approach to target both symptomatic and disease-modifying treatment of cognitive deficits in AD and schizophrenia.

WO2016172547, WO2015028483, WO2011062853 and US2015094328 disclose some M1 PAM compounds. While several M1 PAMs have been disclosed in the literature till date, no drug acting as M1 PAM is launched in the market.

Although the prior arts disclose M1 PAM compounds that are useful in the treatment of CNS related diseases, there exist an issue of poor brain penetration and cholinergic side effects like hypersalivation, diarrhea and emesis. Therefore, there is an un-met need and scope to discover and develop new M1 PAMs with good brain penetration and with no cholinergic side effects for the treatment of CNS related disorders.

SUMMARY OF THE INVENTION

In first aspect, the present invention relates to M1 PAMs of compound of formula (I),

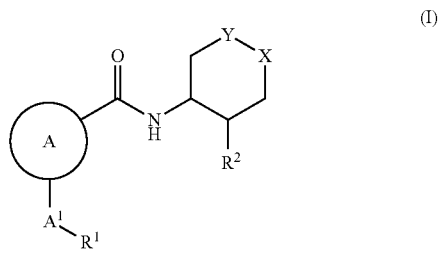

or an isotopic form, a stereoisomer, a tautomer or a pharmaceutically acceptable salt thereof
wherein:
$R^1$ is —$(C_{6-10})$-aryl, —$(C_{5-10})$-heteroaryl or —$(C_{5-10})$-heterocyclyl; each of which is optionally substituted with one or more substituents selected from halogen, —OH, —O—$(C_{1-6})$-alkyl, —S—$(C_{1-6})$-alkyl, —N(CH$_3$)$_2$, —$(C_{1-6})$-alkyl, —$(C_{3-6})$-cycloalkyl, halo$(C_{1-6})$-alkyl, —NH$_2$, —CN and $R^{1a}$;

$R^{1a}$ is —$(C_{6-10})$-aryl or —$(C_{5-10})$-heteroaryl; each of which is optionally substituted with one or more substituents selected from the group consisting of halogen, —OH, —NH$_2$, —CN, —O—$(C_{1-6})$-alkyl, —S—$(C_{1-6})$-alkyl, —$(C_{1-6})$-alkyl and —$(C_{3-6})$-cycloalkyl;

$A^1$ is CH$_2$ or CHF;

$R^2$ is hydrogen or OH;

ring A is

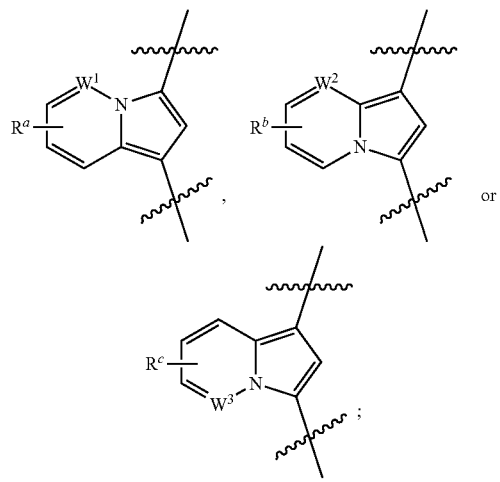

"⁀⁀⁀" represents point of attachment;
$W^1$ is independently selected from C—F or N;
$W^2$ is independently selected from C—F or N;
$W^3$ is independently selected from C—F or N;
$R^a$ is hydrogen, halogen, —OH, —$(C_{1-6})$-alkyl, —O—$(C_{1-6})$-alkyl or halo$(C_{1-6})$-alkyl;
$R^b$ is hydrogen, halogen, —OH, —$(C_{1-6})$-alkyl, —O—$(C_{1-6})$-alkyl or halo$(C_{1-6})$-alkyl;
$R^c$ is hydrogen, halogen, —OH, —$(C_{1-6})$-alkyl, —O—$(C_{1-6})$-alkyl or halo$(C_{1-6})$-alkyl;
X is $CH_2$, O or NH; and Y is $CH_2$, O or NH.

In another aspect, the present invention relates to the processes for preparing the compound of formula (I), or a stereoisomer or a pharmaceutically acceptable salt thereof.

In yet another aspect, the present invention relates to pharmaceutical composition containing a therapeutically effective amount of at least one compound of formula (I), or a stereoisomer or a pharmaceutically acceptable salt thereof and pharmaceutically acceptable excipients or carriers.

In yet another aspect, the present invention relates to compound of formula (I), or a stereoisomer or a pharmaceutically acceptable salt thereof in combination with one or more other therapeutic agents selected from acetylcholinesterase inhibitors and NMDA receptor antagonist.

In yet another aspect, the present invention relates to compound of formula (I), or a stereoisomer or a pharmaceutically acceptable salt thereof, for use as muscarinic M1 receptor positive allosteric modulators.

In yet another aspect, the present invention relates to compound of formula (I), or a stereoisomer or a pharmaceutically acceptable salt thereof, for use in the treatment of disease or disorders selected from cognitive, pain or sleep disorders.

In yet another aspect, the present invention relates to compound of formula (I), or a stereoisomer or a pharmaceutically acceptable salt thereof, for use in the treatment of disease or disorders selected from Alzheimer's disease, schizophrenia or insomnia.

In another aspect, the present invention relates to a method for the treatment of disease or disorders related to muscarinic M1 receptor, comprising administering to a patient in need thereof, a therapeutically effective amount of a compound of formula (I), or a stereoisomer or a pharmaceutically acceptable salt thereof.

In yet another aspect, the present invention relates to use of the compound of formula (I), or a stereoisomer or a pharmaceutically acceptable salt thereof, for the manufacture of a medicament for the treatment of disease or disorders related to muscarinic M1 receptors.

In yet another aspect, the present invention relates to compound of formula (I) or a stereoisomer or a pharmaceutically acceptable salt thereof, for use in positive allosteric modulation of muscarinic M1 receptor.

BRIEF DESCRIPTION OF DRAWINGS

The FIGURE: Effect of test compound (Example 32) in combination with donepezil on hippocampal theta oscillations.

DETAILED DESCRIPTION OF THE INVENTION

Unless otherwise stated, the following terms used in the specification and claims have the meanings given below:

The term, "$(C_{1-6})$-alkyl" as used herein refers to branched or straight chain aliphatic hydrocarbon containing 1 to 6 carbon atoms. Examples of $(C_{1-6})$-alkyl include methyl, ethyl, n-propyl, isopropyl, n-butyl, isobutyl, sec-butyl and tert-butyl. Preferably $(C_{1-6})$-alkyl is methyl, ethyl or isopropyl.

The term, "halogen" or "halo" as used herein refers to fluorine, chlorine, bromine or iodine. Preferably, halogen is fluorine, chlorine or bromine.

The term "halo$(C_{1-6})$-alkyl" as used herein refers to $(C_{1-6})$-alkyl as defined above wherein one or more hydrogen of the same or different carbon atom is substituted with same or different halogens. Examples of halo$(C_{1-6})$-alkyl include fluoromethyl, chloromethyl, fluoroethyl, difluoromethyl, dichloromethyl, trifluoromethyl, difluoroethyl and the like.

The term, "$(C_{3-6})$-cycloalkyl" as used herein refers to saturated monocyclic hydrocarbon ring containing from three to six carbon atoms. Examples of $(C_{3-6})$-cycloalkyl group include cyclopropyl, cyclobutyl, cyclopentyl and cyclohexyl.

The term, "$(C_{6-10})$-aryl" as used herein refers to aromatic hydrocarbon rings containing six to ten carbon atoms. Examples of $(C_{6-10})$-aryl group include phenyl or naphthyl.

The term, "$(C_{5-10})$-heteroaryl" as used herein refers to aromatic monocyclic or aromatic bicyclic heterocycle ring systems containing five to ten atoms. Examples of $(C_{5-10})$-heteroaryl group include 1,2,4-oxadiazolyl, 1,3,4-oxadiazolyl, 1,2,4-thiadiazolyl, 1,3,4-thiadiazolyl, triazolyl, tetrazolyl, triazinyl, furyl, imidazolyl, isoxazolyl, isothiazolyl, oxazolyl, pyrrolyl, pyrazolyl, thiazolyl, thienyl, pyridyl, pyrazinyl, pyrimidinyl, pyridazinyl, benzodioxolyl, benzofuranyl, benzofurazanyl, benzimidazolyl, benzopyrazolyl, benzothiazolyl, benzotriazolyl, benzothiophenyl, benzoxazepinyl, benzooxazinonyl, benzooxazolonyl, benzoxazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, isoquinolyl, quinolyl, phthalazinyl, naphthyridinyl, quinoxalinyl, quinazolinyl, and N-oxides thereof.

The term, "$(C_{5-10})$-heterocyclyl" as used herein refers to non-aromatic monocyclic or non-aromatic bicyclic heterocycle ring systems containing five to ten atoms. Examples of $(C_{5-10})$-heterocyclyl group includes but not limited to piperidinyl, piperazinyl, dihydrobenzofuran, dihydrobenzothiophene, dihydroindole, tetrahydroquinoline and tetrahydroisoquinoline.

The phrase, "therapeutically effective amount" is defined as an amount of a compound of the present invention that (i) treats the particular disease, condition or disorder (ii) eliminates one or more symptoms of the particular disease, condition or disorder (iii) delays the onset of one or more symptoms of the particular disease, condition or disorder described herein.

The term, "isotopic form" as used herein refers to the compound of formula (I) wherein one or more atoms of compound of formula (I) are substituted by their respective isotopes. For example, isotopes of hydrogen include $^2$H (deuterium) and $^3$H (tritium).

The term, "stereoisomers" as used herein refers to isomers of compound of formula (I) that differ in the arrangement of their atoms in space. Compounds disclosed herein may exist as single stereoisomer, racemates and/or mixtures of enantiomers and/or diastereomers. All such single stereoisomer, racemates and mixtures thereof are intended to be within the scope of the present invention.

The term, "pharmaceutically acceptable salt" as used herein refers to salts of the active compound i.e. the compound of formula (I), and are prepared by reaction with the appropriate acid or acid derivative, depending on the particular substituents found on the compounds described herein.

The term, "cognitive disorder" as used herein refers to a group of mental health disorders that principally affect learning, memory, perception, and problem solving, and include amnesia, dementia, and delirium. Cognitive disorders can result due to disease, disorder, ailment or toxicity. Preferably the cognitive disorder is dementia. Example of dementia includes but not limited to, dementia in Alzheimer's disease, dementia in Parkinson's disease, dementia in Huntington's disease, dementia associated with Down syndrome, dementia associated with Tourette's syndrome, dementia associated with post menopause, Frontotemporal dementia, Lewy body dementia, Vascular dementia, dementia in HIV, dementia in Creutzfeldt-Jakob disease, substance-induced persisting dementia, dementia in Pick's disease, dementia in schizophrenia, senile dementia and dementia in general medical conditions.

The term, "patient" as used herein refers to an animal. Preferably the term "patient" refers to mammal. The term mammal includes animals such as mice, rats, dogs, rabbits, pigs, monkeys, horses, pigeons, *Xenopus laevis*, zebrafish, guinea pigs and humans. More preferably the patient is human.

EMBODIMENTS

The present invention encompasses all the compounds described by the compound of formula (I) without any limitation, however, preferred aspects and elements of the invention are discussed herein in the form of the following embodiments.

In one embodiment, the present invention relates to the compound of formula (I), wherein: ring A is

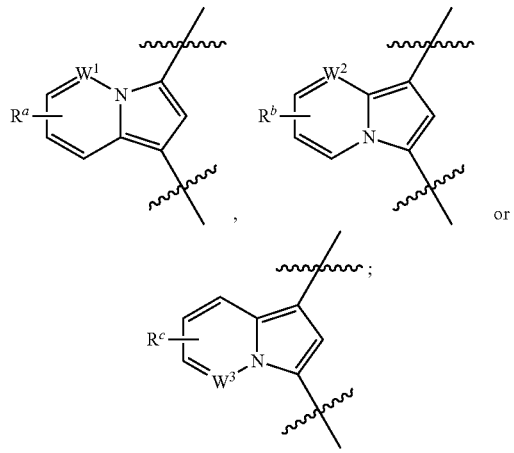

wherein: $W^1$, $W^2$, $W^3$, $R^a$, $R^b$ and $R^c$ are as defined in the first aspect; or an isotopic form, a stereoisomer or a pharmaceutically acceptable salt thereof.

In one embodiment, the present invention relates to the compound of formula (I), wherein: ring A is

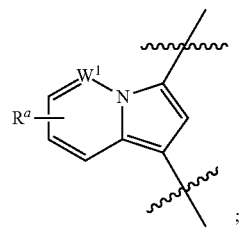

wherein: $W^1$ and $R^a$ are as defined in the first aspect; or an isotopic form, a stereoisomer or a pharmaceutically acceptable salt thereof.

In another embodiment, the present invention relates to the compound of formula (I), wherein: ring A is

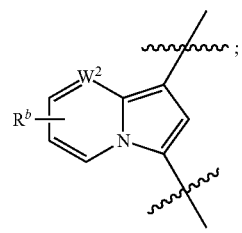

wherein: $W^2$ and $R^b$ is as defined in the first aspect; or an isotopic form, a stereoisomer or a pharmaceutically acceptable salt thereof.

In another embodiment, the present invention relates to the compound of formula (I), wherein: ring A is

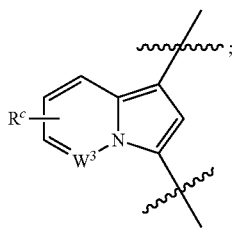

wherein: W³ and R^c is as defined in the first aspect; or an isotopic form, a stereoisomer or a pharmaceutically acceptable salt thereof.

In another embodiment, the present invention relates to the compound of formula (I), wherein: $R^1$ is —$(C_{6-10})$-aryl or —$(C_{5-10})$-heteroaryl; each of which is optionally substituted with one or more substituents selected from halogen, —OH, —O—$(C_{1-6})$-alkyl, —S—$(C_{1-6})$-alkyl, —$N(CH_3)_2$, —$(C_{1-6})$-alkyl, —$(C_{3-6})$-cycloalkyl, halo$(C_{1-6})$-alkyl, —$NH_2$ and —CN or an isotopic form, a stereoisomer or a pharmaceutically acceptable salt thereof.

In another embodiment, the present invention relates to the compound of formula (I), wherein: $R^1$ is —$(C_{6-10})$-aryl or —$(C_{5-10})$-heteroaryl; each of which is substituted with one or more $R^{1a}$; and optionally substituted with one or more substituents selected from halogen, —OH, —O—$(C_{1-6})$-alkyl, —S—$(C_{1-6})$-alkyl, —$N(CH_3)_2$, —$(C_{1-6})$-alkyl, —$(C_{3-6})$-cycloalkyl, halo$(C_{1-6})$-alkyl, —$NH_2$ and —CN or an isotopic form, a stereoisomer or a pharmaceutically acceptable salt thereof.
wherein $R^{1a}$ is as defined in the first aspect; or an isotopic form, a stereoisomer or a pharmaceutically acceptable salt thereof.

In another embodiment, the present invention relates to the compound of formula (I), wherein: $R^1$ is —$(C_{6-10})$-aryl optionally substituted with one or more substituents selected from halogen, —OH, —O—$(C_{1-6})$-alkyl, —S—$(C_{1-6})$-alkyl, —$N(CH_3)_2$, —$(C_{1-6})$-alkyl, —$(C_{3-6})$-cycloalkyl, halo$(C_{1-6})$-alkyl, —$NH_2$ and —CN or an isotopic form, a stereoisomer or a pharmaceutically acceptable salt thereof.

In another embodiment, the present invention relates to the compound of formula (I), wherein: $R^1$ is —$(C_{5-10})$-heteroaryl optionally substituted with one or more substituents selected from halogen, —OH, —O—$(C_{1-6})$-alkyl, —S—$(C_{1-6})$-alkyl, —$N(CH_3)_2$, —$(C_{1-6})$-alkyl, —$(C_{3-6})$-cycloalkyl, halo$(C_{1-6})$-alkyl, —$NH_2$ and —CN or an isotopic form, a stereoisomer or a pharmaceutically acceptable salt thereof.

In another embodiment, the present invention relates to the compound of formula (I), wherein: $R^1$ is —$(C_{5-10})$-heterocyclyl optionally substituted with one or more substituents selected from halogen, —OH, —O—$(C_{1-6})$-alkyl, —S—$(C_{1-6})$-alkyl, —$N(CH_3)_2$, —$(C_{1-6})$-alkyl, —$(C_{3-6})$-cycloalkyl, halo$(C_{1-6})$-alkyl, —$NH_2$ and —CN or an isotopic form, a stereoisomer or a pharmaceutically acceptable salt thereof.

In another embodiment, the present invention relates to the compound of formula (I), wherein: $R^1$ is —$(C_{6-10})$-aryl substituted with one or more $R^{1a}$;
wherein $R^{1a}$ is as defined in the first aspect; or an isotopic form, a stereoisomer or a pharmaceutically acceptable salt thereof.

In another embodiment, the present invention relates to the compound of formula (I), wherein: $R^1$ is —$(C_{5-10})$-heteroaryl substituted with one or more $R^{1a}$;
wherein $R^{1a}$ is as defined in the first aspect; or an isotopic form, a stereoisomer or a pharmaceutically acceptable salt thereof.

In another embodiment, the preferred compound of the invention is selected from the group consisting of:
N-(cis-1S,2S-2-Hydroxycyclohexyl)-5-(4-bromobenzyl)-pyrrolo[1,2-b]pyridazine-7-carboxamide;
N-(cis-1S,2S-2-Hydroxycyclohexyl)-5-(5-bromo-2-fluorobenzyl)-pyrrolo[1,2-b]pyridazine-7-carboxamide;
N-(cis-1S,2S-2-Hydroxycyclohexyl)-5-(4-bromo-3-fluorobenzyl)-pyrrolo[1,2-b]pyridazine-7-carboxamide;
N-(cis-1S,2S-2-Hydroxycyclohexyl)-5-(2,3-dihydrobenzofuran-5-ylmethyl)-pyrrolo[1,2-b]pyridazine-7-carboxamide;
N-(cis-1S,2S-2-Hydroxycyclohexyl)-5-(2-bromo-pyridin-5-ylmethyl)-pyrrolo[1,2-b]pyridazine-7-carboxamide;
N-(cis-1S,2S-2-Hydroxycyclohexyl)-5-(3-methoxybenzyl)-pyrrolo[1,2-b]pyridazine-7-carboxamide;
N-(cis-1S,2S-2-Hydroxycyclohexyl)-5-(2,4-difluorobenzyl)-pyrrolo[1,2-b]pyridazine-7-carboxamide;
N-(cis-1S,2S-2-Hydroxycyclohexyl)-5-(4-fluorobenzyl)-pyrrolo[1,2-b]pyridazine-7-carboxamide;
N-(cis-1S,2S-2-Hydroxycyclohexyl)-5-(2,3-difluorobenzyl)-pyrrolo[1,2-b]pyridazine-7-carboxamide;
N-(cis-1S,2S-2-Hydroxycyclohexyl)-5-(3-fluoro-4-methoxybenzyl)-pyrrolo[1,2-b]pyridazine-7-carboxamide;
N-(cis-1S,2S-2-Hydroxycyclohexyl)-5-(2-chloro-pyridin-4-ylmethyl)-pyrrolo[1,2-b]pyridazine-7-carboxamide;
N-(cis-1S,2S-2-Hydroxycyclohexyl)-5-(4-fluoro-3-methoxybenzyl)-pyrrolo[1,2-b]pyridazine-7-carboxamide;
N-(cis-1S,2S-2-Hydroxycyclohexyl)-5-(2-fluorobenzyl)-pyrrolo[1,2-b]pyridazine-7-carboxamide;
N-(cis-1S,2S-2-Hydroxycyclohexyl)-5-(2-fluoro-4-methoxybenzyl)-pyrrolo[1,2-b]pyridazine-7-carboxamide;
N-(cis-1S,2S-2-Hydroxycyclohexyl)-5-(3,4-difluorobenzyl)-pyrrolo[1,2-b]pyridazine-7-carboxamide;
N-(cis-1S,2S-2-Hydroxycyclohexyl)-5-(2-chloro-pyridin-5-ylmethyl)-pyrrolo[1,2-b]pyridazine-7-carboxamide;
N-(Tetrahydropyran-4-yl)-5-(2-chloropyridin-5-ylmethyl)-pyrrolo[1,2-b]pyridazine-7-carboxamide;
N-(cis-1S,2S-2-Hydroxycyclohexyl)-5-(2-fluoro-3-methoxybenzyl)-pyrrolo[1,2-b]pyridazine-7-carboxamide;
N-(cis-1S,2S-2-Hydroxycyclohexyl)-5-(3-fluorobenzyl)-pyrrolo[1,2-b]pyridazine-7-carboxamide;
N-(cis-1S,2S-2-Hydroxycyclohexyl)-5-(4-methoxybenzyl)-pyrrolo[1,2-b]pyridazine-7-carboxamide;
N-(cis-1S,2S-2-Hydroxycyclohexyl)-5-(4-pyrazol-1-ylbenzyl)-pyrrolo[1,2-b]pyridazine-7-carboxamide;
N-(Tetrahydropyran-4-yl)-5-(4-pyrazol-1-ylbenzyl)-pyrrolo[1,2-b]pyridazine-7-carboxamide;
N-(cis-1S,2S-2-Hydroxycyclohexyl)-5-(4-thiazol-4-ylbenzyl)-pyrrolo[1,2-b]pyridazine-7-carboxamide
N-(cis-1S,2S-2-Hydroxycyclohexyl)-5-(2-bromo-4-fluorobenzyl)-pyrrolo[1,2-b]pyridazine-7-carboxamide
N-(cis-1S,2S-2-Hydroxycyclohexyl)-5-(2,3-difluoro-4-bromobenzyl)-pyrrolo[1,2-b]pyridazine-7-carboxamide
N-(cis-1S,2S-2-Hydroxycyclohexyl)-5-(3-bromo-4-fluorobenzyl)-pyrrolo[1,2-b]pyridazine-7-carboxamide
N-(cis-1S,2S-2-Hydroxycyclohexyl)-5-(3-bromobenzyl)-pyrrolo[1,2-b]pyridazine-7-carboxamide
N-(cis-1S,2S-2-Hydroxycyclohexyl)-5-(2-chloropyridin-3-ylmethyl)-pyrrolo[1,2-b]pyridazine-7-carboxamide N-(cis-1S,2S-2-Hydroxycyclohexyl)-5-(2-bromopyridin-4-ylmethyl)-pyrrolo[1,2-b]pyridazine-7-carboxamide N-(3-Hydroxytetrahydropyran-4-yl)-5-(3-fluorobenzyl)-pyrrolo[1,2-b]pyridazine-7-carboxamide N-(3-Hydroxytetrahydropyran-4-yl)-5-(4-bromobenzyl)-pyrrolo[1,2-b]pyridazine-7-carboxamide N-(cis-1S,2S-2-Hydroxycyclohexyl)-5-[4-(1-methyl-1H-pyrazol-4-yl)-benzyl]-pyrrolo[1,2-b]pyridazine-7-carboxamide;

N-(cis-1S,2S-2-Hydroxycyclohexyl)-5-[3-fluoro-4-(1-methyl-1H-pyrazol-4-yl)-benzyl]-pyrrolo[1,2-b]pyridazine-7-carboxamide;

N-(cis-1S,2S-2-Hydroxycyclohexyl)-5-[2-fluoro-4-(1-methyl-1H-pyrazol-4-yl)-benzyl]-pyrrolo[1,2-b]pyridazine-7-carboxamide;

N-(cis-1S,2S-2-Hydroxycyclohexyl)-5-[6-(1-methyl-1H-pyrazol-4-yl)-pyridin-3-ylmethyl]-pyrrolo[1,2-b]pyridazine-7-carboxamide;

IUPAC names of example 36 to 40; N-(cis-1S,2S-2-Hydroxycyclohexyl)-5-[2,3-difluoro-4-(1-methyl-1H-pyrazol-4-yl)-benzyl]-pyrrolo[1,2-b]pyridazine-7-carboxamide N-(cis-1S,2S-2-Hydroxycyclohexyl)-5-[4-fluoro-3-(1-methyl-1H-pyrazol-4-yl)-benzyl]-pyrrolo[1,2-b]pyridazine-7-carboxamide N-(cis-1S,2S-2-Hydroxycyclohexyl)-5-[3-(1-methyl-1H-pyrazol-4-yl)-benzyl]-pyrrolo[1,2-b]pyridazine-7-carboxamide N-(3-Hydroxytetrahydropyran-4-yl)-5-[4-(1-methyl-1H-pyrazol-4-yl)-benzyl]-pyrrolo[1,2-b]pyridazine-7-carboxamide N-(cis-1S,2S-2-Hydroxycyclohexyl)-5-[2-(1-methyl-1H-pyrazol-4-yl)-pyridin-4-ylmethyl]-pyrrolo[1,2-b]pyridazine-7-carboxamide N-(cis-1S,2S-2-Hydroxycyclohexyl)-3-(4-bromobenzyl)-8-fluoroindolizine-1-carboxamide;

N-(cis-1S,2S-2-Hydroxycyclohexyl)-3-benzyl-8-fluoroindolizine-1-carboxamide;

N-(cis-1S,2S-2-Hydroxycyclohexyl)-3-(2-chloropyridine-4-ylmethyl)-8-fluoroindolizine-1-carboxamide N-(cis-1S,2S-2-Hydroxycyclohexyl)-3-(4-methoxybenzyl)-8-fluoroindolizine-1-carboxamide N-(cis-1S,2S-2-Hydroxycyclohexyl)-3-(4-thiazol-4-yl-benzyl)-8-fluoroindolizine-1-carboxamide N-(3-Hydroxytetrahydropyran-4-yl)-3-(2-chloropyridine-4-ylmethyl)-8-fluoroindolizine-1-carboxamide N-(3-Hydroxytetrahydropyran-4-yl)-3-(4-methoxybenzyl)-8-fluoroindolizine-1-carboxamide N-(cis-1S,2S-2-Hydroxycyclohexyl)-5-[4-(1-methyl-1H-pyrazol-4-yl)-benzyl]-8-fluoroindolizine-1-carboxamide;

N-(cis-1S,2S-2-Hydroxycyclohexyl)-3-(4-(1-methyl-1H-pyrazol-4-yl)-benzyl)-8-fluoroindolizine-1-carboxamide N-(3-Hydroxytetrahydropyran-4-yl)-3-(4-(1-methyl-1H-pyrazol-4-yl)-benzyl)-8-fluoroindolizine-1-carboxamide;

N-(Tetrahydropyran-4-yl)-3-(4-(1-methyl-1H-pyrazol-4-yl)-benzyl)-8-fluoroindolizine-1-carboxamide; and N-(4-Hydroxytetrahydropyran-3-yl)-3-(4-(1-methyl-1H-pyrazol-4-yl)-benzyl)-8-fluoroindolizine-1-carboxamide or a pharmaceutically acceptable salt thereof.

In another embodiment, the present invention relates to the process of preparation of compound of formula (I) as described herein.

Experimental Procedures:

Scheme-1 depicts general processes for preparation of the compound of formula (I), wherein: T is $—(C_{1-6})$-alkyl, $A^1$ is $CH_2$; ring A, $R^1$, $R^{1a}$, X and Y are as defined above.

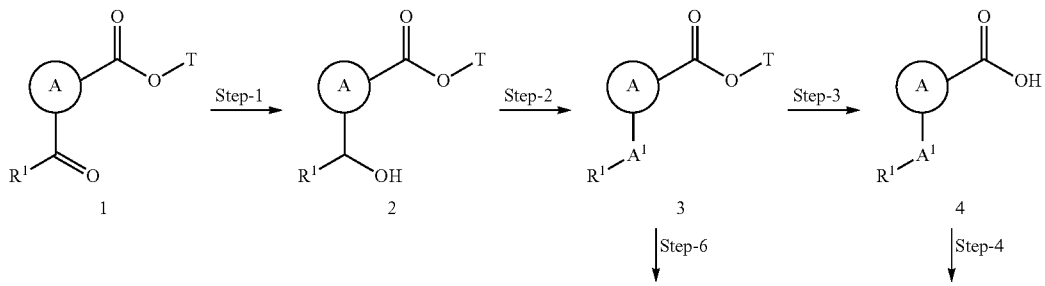

Scheme-1

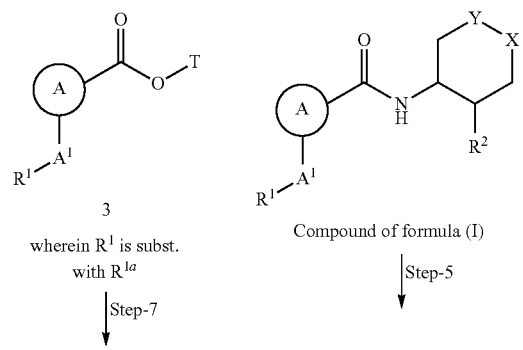

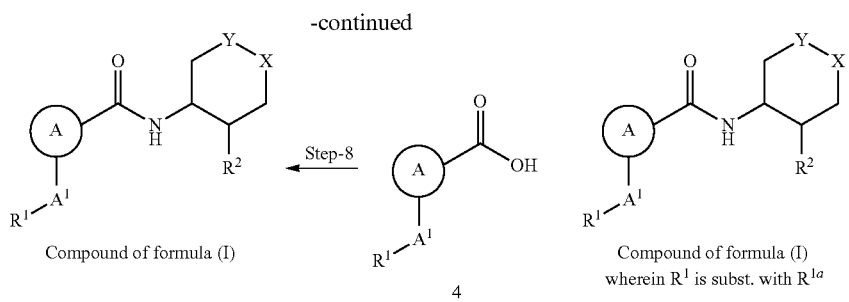

Step-1: Preparation of Compound of Formula 2

The compound of formula 1 is reduced using the reducing agents such as sodium borohydride in a solvent such as methanol, ethanol at the temperature in the range of 25° C. to 30° C. for 1 to 2 hours to obtain the compound of formula 2.

Step-2: Preparation of Compound of Formula 3

The compound of formula 2 is reduced using the reducing agents such as triethyl silane in presence of trifluoroacetic acid at the temperature in the range of −5° C. to 5° C. for 1 to 2 hours to obtain the compound of formula 3.

Step-3: Preparation of Compound of Formula 4

The compound of formula 3 is hydrolyzed to compound of formula 4 in a mixture of solvents such as water and methanol using sodium hydroxide under reflux for 2 to 4 hours.

Step-4: Preparation of Compound of Formula (I)

The compound of formula 4 is coupled with amine, compound of formula 10,

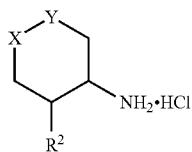

in presence of coupling reagent, HATU, DCC, or EDC and a base, DIPEA in a solvent selected from DMF, THF, dichloromethane or 1,4-dioxane at RT overnight to obtain the compound of formula (I), (wherein R1 is ($C_{6-10}$)-aryl).

Step-5: Preparation of Compound of Formula (I) (Wherein $R^1$ is Substituted with $R^{1a}$)

The compound of formula (I) obtained in step-4 is reacted with $R^{1a}$—B(OH)$_2$ in presence of 1,1'-Bis(diphenylphosphino)ferrocene-palladium(II)dichloride dichloromethane complex in a solvent such as 1,4-dioxane and a base potassium carbonate at a temperature in the range of 90° C. to 110° C. for 2 to 4 hours to obtain the compound of formula (I), (wherein $R^1$ is substituted with $R^{1a}$).

Step-6: Preparation of Compound of Formula 3 (Wherein $R^1$ is Substituted with $R^{1a}$)

The compound of formula 3 obtained in step-2 is reacted with $R^{1a}$—B(OH)$_2$ in presence of 1,1'-Bis(diphenylphosphino)ferrocene-palladium(II)dichloride dichloromethane complex in a solvent such as 1,4-dioxane and a base potassium carbonate at a temperature in the range of 90° C. to 110° C. for 2 to 4 hours to obtain the compound of formula 3, (wherein $R^1$ is substituted with $R^{1a}$).

Step-7: Preparation of Compound of Formula 4

The compound of formula 3, obtained in above step 6 is hydrolyzed to compound of formula 4 in a mixture of solvents such as water and methanol using sodium hydroxide under reflux for 2 to 4 hours.

Step-8: Preparation of Compound of Formula (I)

The compound of formula 4 obtained in step-7 is coupled with amine, compound of formula 10,

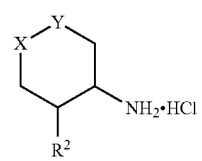

in presence of coupling reagent, HATU, DCC, or EDC and a base, DIPEA in a solvent selected from DMF, THF, dichloromethane or 1,4-dioxane at RT overnight to obtain the compound of formula (I), (wherein R1 is ($C_{6-10}$)-aryl).

Preparation of Pharmaceutically Acceptable Salt of Compound of Formula (I)

The compound of formula (I) can optionally be converted into its pharmaceutically acceptable salt by reaction with the appropriate acid or acid derivative. Suitable pharmaceutically acceptable salts will be apparent to those skilled in the art. The salts are formed with inorganic acids e.g., hydrochloric, hydrobromic, sulfuric, nitric & phosphoric acid or organic acids e.g., oxalic, succinic, maleic, acetic, fumaric, citric, malic, tartaric, benzoic, p-toluic, p-toluenesulfonic, benzenesulfonic acid, methanesulfonic or naphthalenesulfonic acid.

Scheme-2 depicts the alternate general processes for preparation of compound of formula (I), wherein: T is —($C_{1-6}$)-alkyl, $A^1$ is CH$_2$; W$^2$, ring A, $R^1$, $R^{1a}$, $R^2$, X and Y are as defined above.

13

Scheme-2

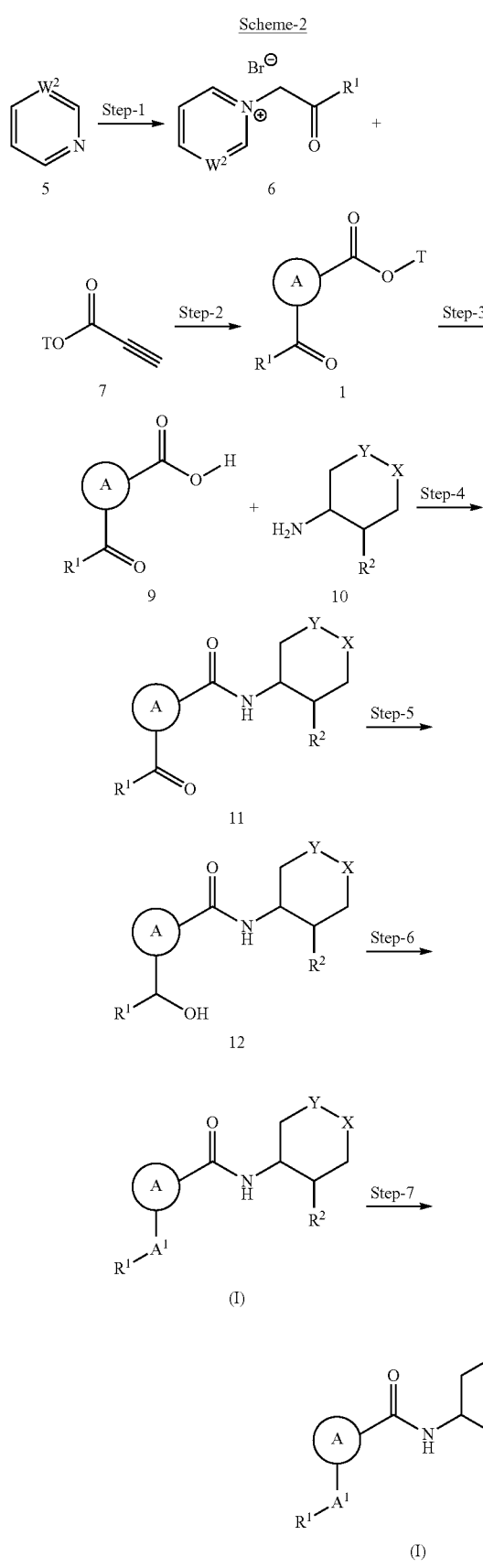

(I)

Step-1: Preparation of Compound of Formula 6

The compound of formula 6 is obtained by reacting the compound of formula 5, with compound of formula A (wherein $R^1$ is as defined above),

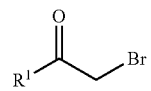

A in a solvent selected from ethyl acetate at the temperature in the range of 25° C. to 30° C. for 14 to 18 hours.

Step-2: Preparation of Compound of Formula 1

The compound of formula 6 is reacted with compound of 7 in presence of a base selected from potassium carbonate in a solvent selected from THF, DCM and ethyl acetate at the temperature in the range of 25° C. to 30° C. for 14 to 18 hours to obtain the compound of formula 1.

Step-3: Preparation of Compound of Formula 9

The compound of formula 1 is hydrolyzed to compound of formula 9 in a mixture of solvents such as water and methanol using sodium hydroxide under reflux for 2 to 4 hours.

Step-4: Preparation of Compound of Formula 11

The compound of formula 9 obtained in step-3 is coupled with amine, compound of formula 10,

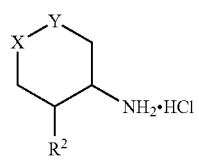

10 in presence of coupling reagent, HATU, DCC, or EDC and a base, DIPEA in a solvent selected from DMF, THF, dichloromethane or 1,4-dioxane at RT overnight to obtain the compound of formula 11.

Step-5: Preparation of Compound of Formula 12

The compound of formula 11 is reduced using the reducing agents such as sodium borohydride in a solvent such as methanol, ethanol at the temperature in the range of 25° C. to 30° C. for 1 to 2 hours to obtain the compound of formula 12.

Step-6: Preparation of Compound of Formula (I) (Wherein $A^1$ is $CH_2$)

The compound of formula 12 is reduced using the reducing agents such as triethyl silane in presence of trifluoroacetic acid at the temperature in the range of −5° C. to 5° C. for 1 to 2 hours to obtain the compound of formula (I) (wherein $A^1$ is $CH_2$).

Step-7: Preparation of Compound of Formula (I) (Wherein $R^1$ is Substituted with $R^{1a}$)

The compound of formula (I) obtained in step-6 is reacted with $R^{1a}$—$B(OH)_2$ in presence of 1,1'-Bis(diphenylphosphino)ferrocene-palladium(II)dichloride dichloromethane complex in a solvent such as 1,4-dioxane and a base potassium carbonate at a temperature in the range of 90° C. to 110° C. for 2 to 4 hours to obtain the compound of formula (I), (wherein $R^1$ is substituted with $R^{1a}$).

Preparation of Pharmaceutically Acceptable Salt of Compound of Formula (I)

The compound of formula (I) can optionally be converted into its pharmaceutically acceptable salt by reaction with the appropriate acid or acid derivative. Suitable pharmaceutically acceptable salts will be apparent to those skilled in the art. The salts are formed with inorganic acids e.g., hydrochloric, hydrobromic, sulfuric, nitric or phosphoric acid or organic acids e.g., oxalic, succinic, maleic, acetic, fumaric, citric, malic, tartaric, benzoic, p-toluic, p-toluenesulfonic, benzenesulfonic acid, methanesulfonic or naphthalene sulfonic acid.

Preparation of Stereoisomers of Compound of Formula (I)

The stereoisomers of compounds of formula (I) may be prepared by one or more conventional ways presented below:

a. One or more of the reagents may be used in their optically active form.
b. Optically pure catalyst or chiral ligands along with metal catalyst may be employed in the reduction process. The metal catalyst may be rhodium, ruthenium, indium and the like. The chiral ligands may preferably be chiral phosphines.
c. The mixture of stereoisomers may be resolved by conventional methods such as forming diastereomeric salts with chiral acids or chiral amines or chiral amino alcohols, or chiral amino acids. The resulting mixture of diastereomers may then be separated by methods such as fractional crystallization, chromatography and the like, which is followed by an additional step of isolating the optically active product from the resolved material/salt.
d. The mixture of stereoisomers may be resolved by conventional methods such as microbial resolution, resolving the diastereomeric salts formed with chiral acids or chiral bases. Chiral acids that can be employed may be tartaric acid, mandelic acid, lactic acid, camphorsulfonic acid, amino acids and the like. Chiral bases that can be employed may be cinchona alkaloids, brucine or a basic amino acid such as lysine, arginine and the like.

In another embodiment, the suitable pharmaceutically acceptable salt includes hydrochloride, hydrobromide, oxalate, fumarate, tartrate, maleate and succinate.

In another aspect of the present invention, the compound of formula (I) are muscarinic M1 positive allosteric modulators.

In another aspect, the present invention relates to a method of treating the disease or disorder selected from cognitive disorder, schizophrenia, pain or sleep disorder, comprising administering to a patient in need thereof, a therapeutically effective amount of compounds of formula (I) or a pharmaceutically acceptable salt thereof.

In another aspect, the present invention relates to a method of treatment of Alzheimer's disease comprising administering to a patient in need thereof, a therapeutically effective amount of compounds of formula (I) or a pharmaceutically acceptable salt thereof.

In another aspect, the present invention relates to a method of treatment of Alzheimer's disease including mild Alzheimer's disease, moderate Alzheimer's disease, severe Alzheimer's disease, mild to moderate Alzheimer's disease or moderate to severe Alzheimer's disease, comprising administering to a patient in need thereof, a therapeutically effective amount of compounds of formula (I) or a pharmaceutically acceptable salt thereof.

In yet another aspect, the present invention relates to compound of formula (I) for use in the treatment of disease or disorder selected from cognitive disorder, schizophrenia, pain or sleep disorder.

In yet another aspect, the present invention relates to use of the compound of formula (I) in the manufacture of medicament for the treatment of diseases or disorder selected from cognitive disorder, schizophrenia, pain or sleep disorder.

In yet another aspect, the present invention relates to use of the compound of formula (I) in the manufacture of medicament for the treatment of diseases or disorder selected from cognitive disorder.

In yet another aspect, the present invention relates to use of the compound of formula (I) in the manufacture of medicament for the treatment of Alzheimer's disease.

In yet another embodiment, the present invention relates to the combination of compound of formula (I) with one or more other therapeutic agents acetylcholinesterase inhibitors and NMDA receptor antagonist.

In another embodiment, the compound of formula (I) of the present invention may be used in combination with one or more other therapeutic agents in the treatment of diseases or disorders for which the compound of formula (I) of the present invention have utility. Examples of the combinations of the compounds of present invention include combination with the therapeutic agents for the treatment of Alzheimer's disease, for example acetylcholinesterase inhibitors such as galantamine, rivastigmine, donepezil, and tacrine; and NMDA receptor antagonist such as memantine.

In yet another embodiment, the present invention relates to combination of compound of formula (I) with at least one therapeutic agents selected from galantamine, rivastigmine, donepezil, tacrine and memantine.

In yet another embodiment the present invention relates to the combination of compound of formula (I) with one or more other therapeutic agents acetylcholinesterase inhibitors and NMDA receptor antagonist for use in the treatment of cognitive disorder, schizophrenia, pain and sleep disorder.

In yet another embodiment the present invention relates to the combination of compound of formula (I) with one or more other therapeutic agents acetylcholinesterase inhibitors and NMDA receptor antagonist for use in the treatment of Alzheimer's disease.

In yet another aspect, the present invention relates to the pharmaceutical composition of the compound of formula (I). In order to use the compound of formula (I), or their stereoisomers and pharmaceutically acceptable salts thereof in therapy, they will normally be formulated into a pharmaceutical composition in accordance with standard pharmaceutical practice.

The pharmaceutical compositions of the present invention may be formulated in a conventional manner using one or more pharmaceutically acceptable excipients. The pharmaceutically acceptable excipients are diluents, disintegrants, binders, lubricants, glidants, polymers, coating agents, solvents, cosolvents, preservatives, wetting agents, thickening agents, antifoaming agents, sweetening agents, flavouring agents, antioxidants, colorants, solubilizers, plasticizer, dispersing agents and the like. Excipients are selected from microcrystalline cellulose, mannitol, lactose, pregelatinized starch, sodium starch glycolate, corn starch or derivatives thereof, povidone, crospovidone, calcium stearate, glyceryl monostearate, glyceryl palmitostearate, talc, colloidal silicone dioxide, magnesium stearate, sodium lauryl sulfate, sodium stearyl fumarate, zinc stearate, stearic acid or hydrogenated vegetable oil, gum arabica, magnesia, glucose, fats, waxes, natural or hardened oils, water, physiological sodium chloride solution or alcohols, for example, ethanol, propanol or glycerol, sugar solutions, such as glucose solutions or mannitol solutions and the like or a mixture of the various excipients.

In yet another aspect, the active compounds of the invention may be formulated in the form of pills, tablets, coated tablets, capsules, powder, granules, pellets, patches, implants, films, liquids, semi-solids, gels, aerosols, emulsions, elixirs and the like. Such pharmaceutical compositions and processes for preparing same are well known in the art.

In yet another aspect, the pharmaceutical composition of the instant invention contains 1 to 90%, 5 to 75% and 10 to 60% by weight of the compounds of the instant invention or pharmaceutically acceptable salt thereof. The amount of the active compounds or its pharmaceutically acceptable salt in the pharmaceutical composition(s) can range from about 1 mg to about 500 mg or from about 5 mg to about 400 mg or from about 5 mg to about 250 mg or from about 7 mg to about 150 mg or in any range falling within the broader range of 1 mg to 500 mg.

The dose of the active compounds can vary depending on factors such as age and weight of patient, nature and severity of the disease to be treated and such other factors. Therefore, any reference regarding pharmacologically effective amount of the compounds of general formula (I), stereoisomers and pharmaceutically acceptable salts thereof refers to the aforementioned factors.

The following abbreviations are used herein:
AMP: Adenosine monophosphate
AUC: Area under the curve
$C_{max}$: Maximum concentration
$CDCl_3$: Deuterated chloroform
DCM: Dichloromethane
DCC: N,N'-Dicyclohexylcarbodiimide
DIPEA: N,N-Diisopropylethylamine
DMF: N,N-Dimethylformamide
DMSO: Dimethyl sulfoxide
$EC_{50}$: Half maximal effective concentration
EDC: Ethylene dichloride
EtOAc: Ethyl acetate
HATU: 2-(7-Aza-1H-benzotriazole-1-yl)-1,1,3,3-tetramethyluronium hexafluorophosphate
HCl: Hydrochloric acid
$H_2O$: Water
h: hour(s)
$H_2SO_4$: Sulfuric acid
$K_2CO_3$: Potassium carbonate
LC-MS/MS: Liquid chromatography-Mass spectrometry/Mass spectrometry
$NaBH_4$: Sodium borohydride
$NaHCO_3$: Sodium bicarbonate
NaOH: Sodium hydroxide
$Na_2SO_4$: Sodium sulphate
$NH_4Cl$: Ammonium chloride
RT: Room temperature (25-30° C.)
ROA: Route of Administration
p.o: Per Oral
T: Temperature
THF: Tetrahydrofuran
$T_{1/2}$: Half-life time

EXAMPLES

The compounds of the present invention were prepared according to the following experimental procedures, using appropriate materials and conditions. The following examples are provided by way of illustration only but not to limit the scope of present invention.

PREPARATION OF INTERMEDIATES

Intermediate 1: 1-(4-Bromophenyl)-prop-2-yn-1-one (I-1)

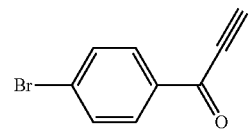

Step 1: Synthesis of 1-(4-bromophenyl)-prop-2-yn-1-ol

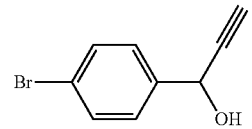

To a stirred solution of 4-bromobenzaldehyde (3.0 g, 16.2 mmols) in dry THF (32.4 mL) cooled at 0° C., a solution of ethynylmagnesium bromide (0.5M, 34.0 mL) was added drop wise over a period of 10 minutes. After 1 hour at 0° C., the reaction mixture was quenched by adding saturated aqueous $NH_4Cl$ solution. The two layers were separated and aqueous layer was extracted with EtOAc. The combined organic layer was washed once with brine solution, dried over anhydrous $Na_2SO_4$ and the solvent was removed under reduced pressure to obtain the title compound.

Yield: 3.7 g; $^1$H-NMR (400 MHz, $CDCl_3$): δ 7.51 (d, J=8.4 Hz, 2H), 7.42 (d, J=8.4 Hz, 2H), 5.41 (s, 1H), 2.66 (s, 1H), 2.24 (bs, 1H); Mass (m/z): 211, 213 $(M+H)^+$.

Step-2: Synthesis of 1-(4-bromophenyl)-prop-2-yn-1-one

To a stirred solution of 1-(4-bromophenyl)-prop-2-yn-1-ol (3.6 g, 17.3 mmols) in acetone (10.0 mL) cooled at 0° C., a solution of chromium trioxide (1.15 g, 11.5 mmols) in a mixture of $H_2O$ (3.5 mL) and $H_2SO_4$ (1.0 mL) was added drop wise. After stirring for 2 hours at RT, the reaction mixture was transferred to separating funnel containing water and chloroform. The two layers were separated and aqueous layer was extracted with $CHCl_3$. The combined organic layer was washed once with brine solution, dried over anhydrous Na$_2$SO$_4$ and the solvent was removed under reduced pressure to obtain the title compound. Yield: 3.1 g (86%); $^1$H-NMR (400 MHz, CDCl$_3$): δ 8.01 (d, J=8.3 Hz, 2H), 7.66 (d, J=8.3 Hz, 2H), 3.44 (s, 1H); Mass (m/z): 209, 211 (M+H)$^+$.

Following the two step protocol as mentioned above, differently substituted aryl ethynyl ketones have been synthesized and used in subsequent reactions to obtain the corresponding final M1 PAM compounds.

Intermediate 2:
1-Ethoxycarbonylmethyl-pyridazin-1-ium bromide
(I-2)

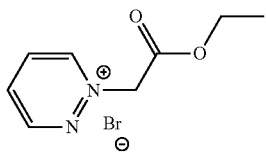

To a stirred solution of pyridazine (1.0 g, 12.5 mmols) in EtOAc (25.0 mL) cooled at 0° C., ethylbromoacetate (1.54 mL, 13.8 mmols) was added drop wise. After stirring for 16 hours at RT, the volatiles were removed under reduced pressure. The solid obtained was triturated with solvent ether, dried under vacuum to obtain the title compound.

Yield: 2.6 g (86%); $^1$H-NMR (400 MHz, DMSO-d$_6$): δ 10.04 (d, 5.7 Hz, 1H), 9.73 (d, J=4.4 Hz, 1H), 8.89 (dd, J=5.7, 7.8 Hz, 1H), 8.76 (dd, J=5.0, 7.8 Hz, 1H), 5.97 (s, 2H), 4.28 (q, 2H), 1.25 (t, J=7.1 Hz, 3H); Mass (m/z): 167.1 (M+H)$^+$.

Example 1

N-(cis-1S,2S-2-Hydroxycyclohexyl)-5-(4-bromobenzyl)-pyrrolo[1,2-b]pyridazine-7-carboxamide

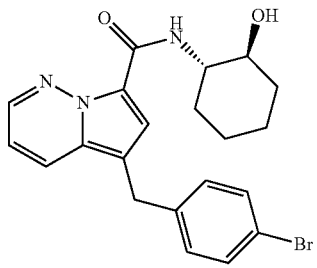 [SMILES: O=C(N[C@H]1CCCC[C@@H]1O)c1cc(Cc2ccc(Br)cc2)c2cccnn12]

Step-1: Synthesis of ethyl 5-(4-bromobenzoyl)-pyrrolo[1,2-b]pyridazine-7-carboxylate To a stirred solution of 1-(4-bromophenyl)-prop-2-yn-1-one (I-1) (3.1 g, 15.0 mmols) in dry THF (60.0 mL) cooled at 0° C., K$_2$CO$_3$ (3.53 g, 25.6 mmols) followed by 1-ethoxycarbonylmethyl-pyridazin-1-ium bromide (I-2) (3.71 g, 15.1 mmols) was added. After stirring for 16 hours at RT, the reaction mixture was diluted with water and EtOAc. The two layers were separated and aqueous layer was extracted with EtOAc. The combined organic layer was washed once with brine solution, dried over anhydrous Na$_2$SO$_4$ and the solvent was removed under reduced pressure to obtain a crude product which was purified by silica gel column chromatography to obtain the title compound.

Yield: 3.4 g (60%); $^1$H-NMR (400 MHz, CDCl$_3$): δ 8.87 (d, 9.0 Hz, 1H), 8.61 (d, J=4.4 Hz, 1H), 7.78 (s, 1H), 7.75 (d, J=8.3 Hz, 2H), 7.69 (d, J=8.3 Hz, 2H), 7.22 (dd, J=4.4, 9.0 Hz, 1H), 4.46 (q, 2H), 1.43 (t, J=7.1 Hz, 3H); Mass (m/z): 373.0, 375.0 (M+H)$^+$.

Step-2: Synthesis of ethyl 5-[(4-bromophenyl)-hydroxymethyl]pyrrolo[1,2-b]pyridazine-7-carboxylate To a stirred solution of ethyl 5-(4-bromobenzoyl)-pyrrolo[1,2-b]pyridazine-7-carboxylate obtained in above step (3.4 g, 9.1 mmols) in ethanol (45.0 mL), NaBH$_4$ (1.04 g, 27.5 mmols) was added at 0° C. After stirring for 2 hours at RT, the reaction mixture was diluted with water and CHCl$_3$. The two layers were separated and aqueous layer was extracted with CHCl$_3$. The combined organic layer was washed with brine solution, dried over anhydrous Na$_2$SO$_4$ and the solvent was removed under reduced pressure to obtain the title compound.

Yield: 3.4 g (100%); $^1$H-NMR (400 MHz, CDCl$_3$): δ 8.37 (d, J=4.4 Hz, 1H), 7.92 (d, J=9.1 Hz, 1H), 7.52 (d, J=8.3 Hz, 2H), 7.35 (d, J=8.3 Hz, 2H), 7.31 (s, 1H), 6.79 (dd, J=4.4, 9.0 Hz, 1H), 6.12 (d, J=3.0 Hz, 1H), 4.42 (q, 2H), 2.29 (d, J=3.0 Hz, 1H), 1.4 (t, J=7.1 Hz, 3H); Mass (m/z): 374.9, 376.9 (M+H)$^+$.

Step 3: Synthesis of ethyl 5-(4-bromobenzyl)-pyrrolo[1,2-b]pyridazine-7-carboxylate To a stirred solution of ethyl 5-[(4-bromophenyl)-hydroxymethyl]pyrrolo[1,2-b]pyridazine-7-carboxylate obtained in above step (3.4 g, 9.1 mmols) in trifluoroacetic acid (7.1 mL), triethylsilane (3.2 mL, 20.3 mmols) was added at −10° C. After stirring for 1 hour at 0° C., the reaction mixture was diluted with 10% aq. NaHCO$_3$ solution and EtOAc. The two layers were separated and aqueous layer was extracted with CHCl$_3$. The combined organic layer was washed with brine solution, dried over anhydrous Na$_2$SO$_4$ and the solvent was removed under reduced pressure to obtain a crude product which was purified by silica gel column chromatography to obtain the title compound.

Yield: 1.96 g (59%); $^1$H-NMR (400 MHz, CDCl$_3$): δ 8.34 (d, J=4.4 Hz, 1H), 7.69 (d, J=7.8 Hz, 1H), 7.42 (d, J=8.1 Hz, 2H), 7.34 (s, 1H), 7.08 (d, J=8.1 Hz, 2H), 6.74 (dd, J=4.4 Hz, 9.0 Hz, 1H), 4.43 (q, 2H), 4.05 (s, 2H), 1.41 (t, 3H); Mass (m/z): 358.8, 360.8 (M+H)$^+$.

Step 4: Synthesis of 5-(4-bromobenzyl)-pyrrolo[1,2-b]pyridazine-7-carboxylic acid To a stirred solution of ethyl 5-(4-bromobenzyl)-pyrrolo[1,2-b]pyridazine-7-carboxylate obtained in above step (0.029 g, 0.08 mmol) in 2:1 mixture of H$_2$O and ethanol (1.0 mL), NaOH (0.0065 g, 0.16 mmol) was added at 0° C. After stirring for 2 hours at reflux temperature, the reaction mixture was cooled to RT, acidified with 2N HCl and extracted with DCM. The combined organic layer was washed with brine solution, dried over anhydrous Na$_2$SO$_4$ and the solvent was removed under reduced pressure to obtain the title compound.

Yield: 0.034 g (100%); $^1$H-NMR (400 MHz, CDCl$_3$): δ 12.0 (bs, 1H), 8.26 (d, J=4.4 Hz, 1H), 7.81 (d, J=7.8 Hz, 1H), 7.53 (s, 1H), 7.42 (d, J=8.1 Hz, 2H), 7.08 (d, J=8.1 Hz, 2H), 6.83 (dd, J=4.4 Hz, 9.0 Hz, 1H), 4.08 (s, 2H); Mass (m/z): 331.2, 333.3 (M+H)$^+$.

Step 5: Synthesis of N-(cis-1S,2S-2-hydroxycyclohexyl)-5-(4-bromobenzyl)-pyrrolo[1,2-b]pyridazine-7-carboxamide To a stirred solution of 5-(4-bromobenzyl)-pyrrolo[1,2-b]pyridazine-7-carboxylic acid obtained in above step (34 mg, 0.1 mmol) in DCM (1.1 mL), DIPEA (0.05 mL, 0.3 mmol), 1-aminocyclohexanol hydrochloride (15.6 mg, 0.1 mmol) and TBTU (36.0 mg, 0.11 mmol) were added in sequence at 0° C. After stirring for 16 hour at RT, the reaction mixture was diluted with water and DCM. The two layers were separated and aqueous layer was extracted with DCM. The combined organic layer was washed with brine solution, dried over anhydrous Na$_2$SO$_4$ and the solvent was removed under reduced pressure to obtain a crude product which was purified by silica gel column chromatography to obtain the title compound.

Yield: 37.0 mg (86%); $^1$H-NMR (400 MHz, CDCl$_3$): δ 9.01 (d, J=6.3 Hz, 1H), 8.18 (d, J=4.1 Hz, 1H), 7.24 (d, J=8.9 Hz, 1H), 7.53 (s, 1H), 7.39 (d, J=8.3 Hz, 2H), 7.07 (d, J=8.3 Hz, 2H), 6.7 (dd, 4.1, 8.9 Hz, 1H), 4.11 (d, J=3.1 Hz, 1H), 4.06 (s, 2H), 3.94-3.90 (m, 1H), 3.53-3.48 (m, 1H), 2.14-2.10 (m, 2H), 1.78-168 (m, 2H), 1.48-1.35 (m, 4H); Mass (m/z): 428.2, 430.4 (M+H)$^+$.

The following Example 2 to Example 31 were prepared by following the experimental procedure as described in Example 1 using substituted aryl ethynyl ketones and intermediate I-2 with some non-critical variations.

| Ex. No | Chemical Structure | Analytical Characterization |
| --- | --- | --- |
| Example 2 | 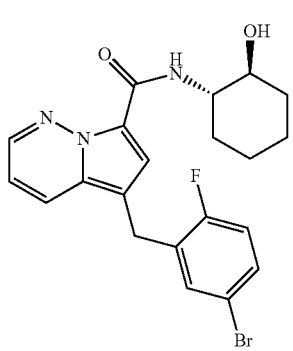 [SMILES: O=C(N[C@H]1CCCC[C@@H]1O)c1cc(Cc2cc(Br)ccc2F)c2cccnn12]<br>N-(cis-1S,2S-2-Hydroxycyclohexyl)-5-(5-bromo-2-fluorobenzyl)-pyrrolo[1,2-b]pyridazine-7-carboxamide | $^1$H-NMR (400 MHz, CDCl$_3$): δ 9.02 (d, J = 6.3 Hz, 1H) 8.20 (d, J = 3.4 Hz, 1H), 7.88 (d, J = 8.9 Hz, 1H), 7.54 (s, 1H), 7.31-7.23 (m 2H), 6.94 (t, J = 9.0 Hz, 1H), 6.76 (dd, 9.0 Hz, 4.4 Hz, 1H), 4.07 (s, 2H), 3.96-3.88 (m, 1H), 3.54-3.48 (m, 1H), 2.13-2.07 (m, 2H), 1.78-1.75 (m, 2H), 1.51-1.30 (m, 4H); Mass (m/z): 446.1, 448 (M + H)$^+$. |
| Example 3 | 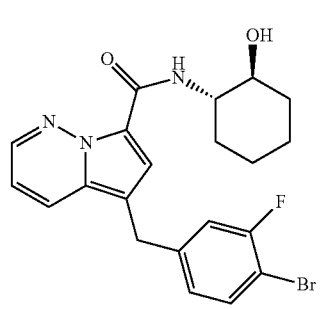 [SMILES: O=C(N[C@H]1CCCC[C@@H]1O)c1cc(Cc2ccc(Br)c(F)c2)c2cccnn12]<br>N-(cis-1S,2S-2-Hydroxycyclohexyl)-5-(4-bromo-3-fluorobenzyl)-pyrrolo[1,2-b]pyridazine-7-carboxamide | $^1$H-NMR (400 MHz, CDCl$_3$): δ 8.99 (d, J = 6.3 Hz, 1H), 8.18 (d, J = 4.2 Hz, 1H), 7.73 (d, J = 9.3 Hz, 1H), 7.5 (s, 1H), 7.43 (t, J = 7.7 Hz, 1H), 6.9 (d, J = 9.4 Hz, 1H), 6.86 (d, J = 8.3 Hz, 1H), 6.71 (dd, J = 8.7 Hz, 4.4 Hz, 1H), 4.04 (d, 2H), 3.95-3.87 (m, 1H) 3.53-3.46 (m, 1H), 2.12-2.06 (m, 2H), 1.71-1.74 (m, 2H), 1.46-1.23 (m, 4H); Mass (m/z): 446.0, 448.1 (M + H)$^+$. |

-continued

| Ex. No | Chemical Structure | Analytical Characterization |
|---|---|---|
| Example 4 | 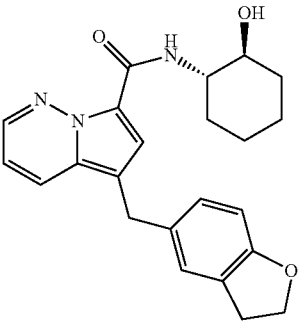 [SMILES: O=C(N[C@H]1CCCC[C@@H]1O)c1cc(Cc2ccc3c(c2)CCO3)c2cccnn12]<br>N-(cis-1S,2S-2-Hydroxycyclohexyl)-5-(2,3-dihydrobenzofuran-5-ylmethyl)-pyrrolo[1,2-b]pyridazine-7-carboxamide | $^1$H-NMR (400 MHz, CDCl$_3$): δ 9.04 (d, J = 6.3 Hz, 1H) 8.16 (d, J = 3.2 Hz, 1H), 7.79 (d, J = 9.2 Hz, 1H), 7.54 (s, 1H), 7.0 (s, 1H), 6.96 (d, J = 8.2 Hz, 1H) 6.69-6.65 (m, 2H), 4.55 (t, J = 8.6 Hz, 2H), 4.21 (d, J = 3.3 Hz, 1H), 4.03 (s, 2H), 3.95-3.89 (m, 1H) 3.54-3.48 (m, 1H), 3.16 (t, J = 8.6 Hz, 2H), 2.14-2.07 (m, 2H), 1.79-1.76 (m, 2H), 1.55-1.25 (m, 4H); Mass (m/z): 392.0 (M + H)$^+$. |
| Example 5 | 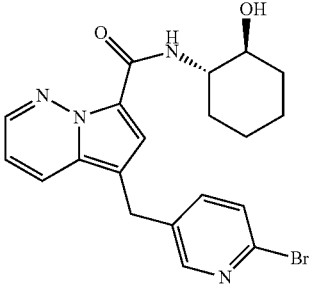 [SMILES: O=C(N[C@H]1CCCC[C@@H]1O)c1cc(Cc2ccc(Br)nc2)c2cccnn12]<br>N-(cis-1S,2S-2-Hydroxycyclohexyl)-5-(2-bromo-pyridin-5-ylmethyl)-pyrrolo[1,2-b]pyridazine-7-carboxamide | $^1$H-NMR (400 MHz, CDCl$_3$): δ 8.99 (d, J = 6.2 Hz, 1H), 8.28 (s, 1H), 8.21 (d, J = 3.4 Hz, 1H), 7.76 (d, J = 9.0 Hz, 1H), 7.52 (s, 1H), 7.38 (d, J = 8.1 Hz, 1H), 7.35 (d, J = 8.1 Hz, 1H), 6.75 (dd, J = 9.0 Hz, 4.4 Hz, 1H), 4.08 (s, 2H), 4.03 (d, J = 3.4 Hz, 1H), 3.97-3.89 (m, 1H), 3.53-3.48 (m, 1H), 2.13-2.08 (m, 2H), 1.79-1.76 (m, 2H), 1.51-1.27 (m, 4H); Mass (m/z): 429, 431.1 (M + H)$^+$. |
| Example 6 | 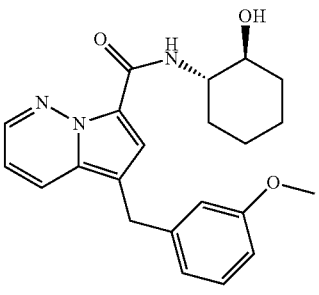 [SMILES: COc1cccc(Cc2cc(C(=O)N[C@H]3CCCC[C@@H]3O)n3ncccc23)c1]<br>N-(cis-1S,2S-2-Hydroxycyclohexyl)-5-(3-methoxybenzyl)-pyrrolo[1,2-b]pyridazine-7-carboxamide | $^1$H-NMR (400 MHz, CDCl$_3$): δ 9.03 (d, J = 6.3 Hz, 1H), 8.17 (d, J = 4.2 Hz, 1H), 7.78 (d, J = 9.2 Hz, 1H), 7.56 (s, 1H), 7.21 (t, J = 7.6 Hz, 1H), 6.8 (d, J = 7.5 Hz, 1H), 6.75-6.72 (m, 2H), 6.68 (dd, J = 9.0 Hz, 4.4 Hz, 1H), 4.2 (d, J = 3.5 Hz, 1H), 4.09 (s, 2H), 3.95-3.9 (m, 1H), 3.75 (s, 3H), 3.54-3.49 (m, 1H), 2.14-2.07 (m, 2H), 1.79-1.76 (m, 2H), 1.45-1.25 (m, 4H); Mass (m/z): 380.1 (M + H)$^+$. |

| Ex. No | Chemical Structure | Analytical Characterization |
|---|---|---|
| Example 7 | 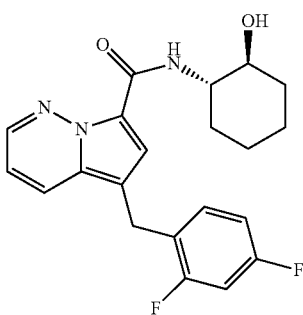 [SMILES: O=C(N[C@H]1CCCC[C@@H]1O)c1cc(Cc2ccc(F)cc2F)c2cccnn12]<br>N-(cis-1S,2S-2-Hydroxycyclohexyl)-5-(2,4-difluorobenzyl)-pyrrolo[1,2-b]pyridazine-7-carboxamide | $^1$H-NMR (400 MHz, CDCl$_3$): δ 9.01 (d, J = 4.7 Hz, 1H), 8.19 (t, J = 1.2 Hz, 1H), 7.88 (d, J = 8.9 Hz, 1H), 7.53 (s, 1H), 7.14-4.08 (m, 1H), 6.81-6.71 (m, 3H), 4.14 (d, J = 2.8 Hz, 1H), 4.07 (s, 2H), 3.96-3.88 (m, 1H), 3.53-3.47 (m, 1H), 2.13-2.06 (m, 2H), 1.78-1.75 (m, 2H), 1.51-1.25 (m, 4H); Mass (m/z): 386.1 (M + H)$^+$. |
| Example 8 | 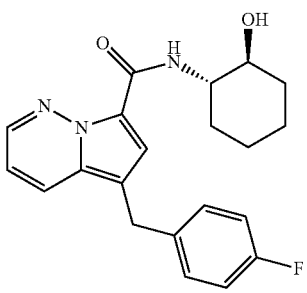 [SMILES: O=C(N[C@H]1CCCC[C@@H]1O)c1cc(Cc2ccc(F)cc2)c2cccnn12]<br>N-(cis-1S,2S-2-Hydroxycyclohexyl)-5-(4-fluorobenzyl)-pyrrolo[1,2-b]pyridazine-7-carboxamide | $^1$H-NMR (400 MHz, CDCl$_3$): δ 9.02 (6.3 Hz, 1H), 8.18 (d, J = 4.4 Hz, 1H), 7.76 (d, J = 9.0 Hz, 1H), 7.53 (s, 1H), 7.16-7.12 (m, 2H), 6.97 (t, J = 8.6 Hz, 2H), 6.7 (dd, J = 4.4, 9.0 Hz, 1H), 4.14 (s, 1H), 4.08 (s, 2H), 3.96-3.89 (m, 1H), 3.53-3.49 (m, 1H), 2.14-2.07 (m, 2H), 1.79-1.76 (m, 2H), 1.48-1.25 (m, 4H); Mass (m/z): 368.3 (M + H)$^+$. |
| Example 9 | 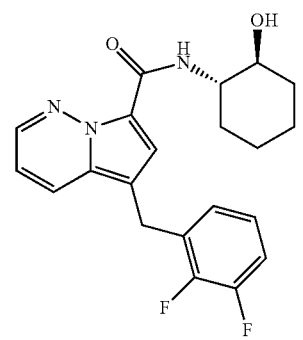 [SMILES: O=C(N[C@H]1CCCC[C@@H]1O)c1cc(Cc2cccc(F)c2F)c2cccnn12]<br>N-(cis-1S,2S-2-Hydroxycyclohexyl)-5-(2,3-difluorobenzyl)-pyrrolo[1,2-b]pyridazine-7-carboxamide | $^1$H-NMR (400 MHz, CDCl$_3$): δ 9.01 (d, J = 6.3 Hz, 1H), 8.19 (d, J = 4.4 Hz, 1H), (7.91 (d, J = 9.0 Hz, 1H), 7.5 (s, 1H), 7.03-6.9 (m, 3H), 6.9 (dd, J = 4.4, 9.0 Hz, 1H), 4.13 (s, 3H), 3.96-3.88 (m, 1H), 3.52-3.5 (m, 1H), 2.13-2.06 (m, 2H), 1.78-1.75 (m, 2H), 1.50-1.27 (m, 4H); Mass (m/z): 386.1 (M + H)$^+$. |

| Ex. No | Chemical Structure | Analytical Characterization |
| --- | --- | --- |
| Example 10 | N-(cis-1S,2S-2-Hydroxycyclohexyl)-5-(3-fluoro-4-methoxybenzyl)-pyrrolo[1,2-b]pyridazine-7-carboxamide | $^1$H-NMR (400 MHz, CDCl$_3$): δ 9.0 (d, J = 6.08 Hz, 1H), 8.16 (d, J = 3.1 Hz, 1H), 7.74 (d, J = 8.9 Hz, 1H), 7.51 (s, 1H), 6.88-6.81 (m, 3H), 6.68 (dd, J = 4.4 Hz, 8.9 Hz, 1H), 4.02 (s, 2H), 3.94-3.89 (m, 1H), 3.83 (s, 3H), 3.52-3.46 (m, 1H), 2.15-2.05 (m, 2H), 1.76-1.74 (m, 2H), 1.49-1.23 (m, 4H); Mass (m/z): 398.1 (M + H)$^+$. |
| Example 11 | N-(cis-1S,2S-2-Hydroxycyclohexyl)-5-(2-chloro-pyridin-4-ylmethyl)-pyrrolo[1,2-b]pyridazine-7-carboxamide | $^1$H-NMR (400 MHz, CDCl$_3$): δ 9.0 (d, J = 6.4 Hz, 1H), 8.27-8.23 (m, 2H), 7.76 (d, J = 9.2 Hz, 1H), 7.56 (s, 1H), 7.13 (s, 1H), 7.05 (d, J = 4.9 Hz, 1H), 6.7 (d, J = 9.0 Hz, 1H), 4.11 (s, 2H), 3.98-3.93 (m, 2H), 3.52 (bs, 1H), 2.15-2.1 (m, 2H), 1.8-1.77 (m, 2H), 1.49-1.32 (m, 4H); Mass (m/z): 385.1 (M + H)$^+$. |
| Example 12 | N-(cis-1S,2S-2-Hydroxycyclohexyl)-5-(4-fluoro-3-methoxybenzyl)-pyrrolo[1,2-b]pyridazine-7-carboxamide | $^1$H-NMR (400 MHz, CDCl$_3$): δ 9.03 (d, J = 6.3 Hz, 1H), 8.19 (d, J = 4.1 Hz, 1H), 7.52 (d, J = 8.9 Hz, 1H), 7.55 (s, 1H), 6.99-6.94 (m, 1H), 6.78 (d, J = 8.04 Hz, 1H), 6.73-6.67 (m, 2H), 4.13 (d, J = 3.6 Hz, 1H), 4.07 (s, 2H), 3.96-3.89 (m, 1H) 3.81 (s, 3H), 3.55-3.48 (m, 1H), 2.14-2.08 (m, 2H), 1.79-1.76 (m, 2H), 1.49-1.28 (m, 4H); Mass (m/z): 398.1 (M + H)$^+$. |

| Ex. No | Chemical Structure | Analytical Characterization |
|---|---|---|
| Example 13 | 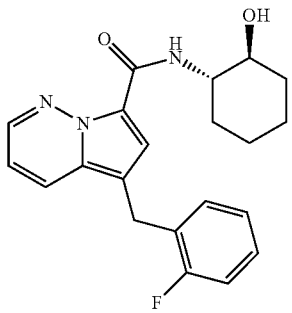 [SMILES: O=C(N[C@H]1CCCC[C@@H]1O)c1cc(Cc2ccccc2F)c2cccnn12]<br>N-(cis-1S,2S-2-Hydroxycyclohexyl)-5-(2-fluorobenzyl)-pyrrolo[1,2-b]pyridazine-7-carboxamide | $^1$H-NMR (400 MHz, CDCl$_3$): δ 9.01 (s, 1H), 8.16 (s, 1H), 7.90 (d, J = 8.9 Hz, 1H), 7.55 (s, 1H), 7.16 (m, 2H), 7.03-7.0 (m, 2H), 6.72 (dd, J = 7.3 Hz, 2.8 Hz, 1H), 4.17 (s, 1H), 4.11 (s, 2H), 3.91-3.90 (m, 1H), 3.50 (m, 1H), 2.13-2.06 (m, 2H), 1.78-1.75 (m, 2H), 1.50-1.27 (m, 4H); Mass (m/z): 368.2 (M + H)$^+$. |
| Example 14 | 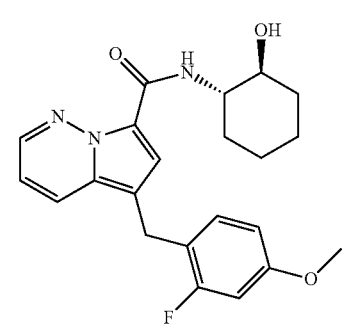 [SMILES: COc1ccc(Cc2cc(C(=O)N[C@H]3CCCC[C@@H]3O)n3ncccc23)c(F)c1]<br>N-(cis-1S,2S-2-Hydroxycyclohexyl)-5-(2-fluoro-4-methoxybenzyl)-pyrrolo[1,2-b]pyridazine-7-carboxamide. | $^1$H-NMR (400 MHz, CDCl$_3$): δ 9.02 (d, J = 6.08 Hz, 1H), 8.17 (d, J = 4.24 Hz, 1H), 7.88 (d, J = 9.0 Hz, 1H), 7.53 (s, 1H), 7.07 (t, J = 8.4 Hz, 1H), 6.71 (dd, J = 9.0 Hz, 4.4 Hz, 1H), 6.4 (d, J = 9.5 Hz, 2H), 4.38 (s, 1H), 4.03 (s, 2H), 3.98-3.87 (m, 1H), 3.76 (s, 3H), 3.52-3.50 (m, 1H), 2.13-2.06 (m, 2H), 1.78-1.75 (m, 2H), 1.50-1.26 (m, 4H); Mass (m/z): 398.1 (M + H)$^+$. |
| Example 15 | 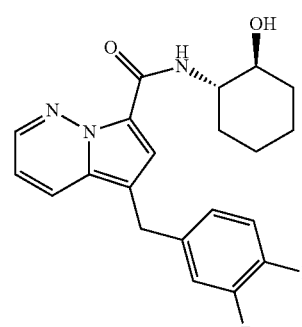<br>N-(cis-1S,2S-2-Hydroxycyclohexyl)-5-(3,4-difluorobenzyl)-pyrrolo[1,2-b]pyridazine-7-carboxamide | $^1$H-NMR (400 MHz, CDCl$_3$): δ 9.01 (d, J = 5.1 Hz, 1H), 8.20 (d, J = 3.7 Hz, 1H), 7.75 (d, J = 9.0 Hz, 1H), 7.53 (s, 1H), 7.14-7.04 (m, 1H), 7.02-6.91 (m, 2H), 6.72 (dd, J = 9.0 Hz, 4.4 Hz, 1H), 4.13-4.07 (m, 3H), 3.94-3.89 (m, 1H), 3.54-3.49 (m, 1H), 2.36-2.28 (m, 2H), 1.79-1.76 (m, 2H), 1.51-1.25 (m, 4H); Mass (m/z): 386.1 (M + H)$^+$. |

-continued

| Ex. No | Chemical Structure | Analytical Characterization |
|---|---|---|
| Example 16 | 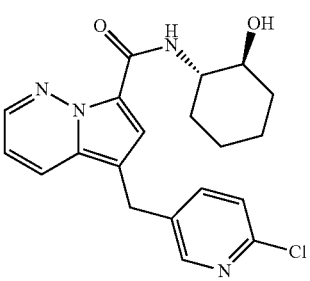 [SMILES: O=C(N[C@H]1CCCC[C@@H]1O)c1cc(Cc2ccc(Cl)nc2)c2cccnn12]<br>N-(cis-1S,2S-2-Hydroxycyclohexyl)-5-(2-chloro-pyridin-5-ylmethyl)-pyrrolo[1,2-b]pyridazine-7-carboxamide | $^1$H-NMR (400 MHz, CDCl$_3$): δ 9.0 (d, J = 6.4 Hz, 1H), 8.29 (d, J = 1.8 Hz, 1H), 8.22 (d, J = 4.1 Hz, 1H), 7.77 (d, J = 9.0 Hz, 1H), 7.53 (s, 1H), 7.43 (d, J = 8.1 Hz 1H), 7.23 (d, J = 8.1 Hz, 1H), 6.75 (dd, J = 9.1 Hz, 4.5 Hz, 1H), 4.10 (s, 2H), 4.03 (bs, 1H), 3.97-3.89 (m, 1H), 3.54-3.51 (m, 1H), 2.14-2.08 (m, 2H), 1.79-1.76 (m, 2H), 1.51-1.25 (m, 4H); Mass (m/z): 385.0, 387.0 (M + H)$^+$. |
| Example 17 | 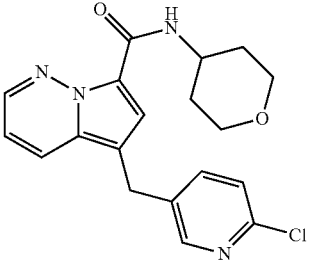 [SMILES: O=C(NC1CCOCC1)c1cc(Cc2ccc(Cl)nc2)c2cccnn12]<br>N-(Tetrahydropyran-4-yl)-5-(2-chloropyridin-5-ylmethyl)-pyrrolo[1,2-b]pyridazine-7-carboxamide | $^1$H-NMR (400 MHz, CDCl$_3$): δ 8.91 (d, J = 8.0 Hz, 1H), 8.29 (d, J = 1.92 Hz, 1H), 8.21 (d, J = 3.2 Hz, 1H), 7.76 (d, J = 8.8 Hz, 1H), 7.52 (s, 1H), 7.44 (d, J = 8.1 Hz, 1H), 7.22 (d, J = 8.2 Hz, 1H), 6.73 (dd, J = 9.0, 4.4 Hz, 1H), 4.33-4.29 (m, 1H), 4.09 (s, 2H), 4.02-3.97 (m, 2H), 3.61-3.55 (m, 2H), 2.06-2.03 (m, 2H), 1.71-1.65 (m, 2H); Mass (m/z): 371.1, 373.1 (M + H)$^+$. |
| Example 18 | 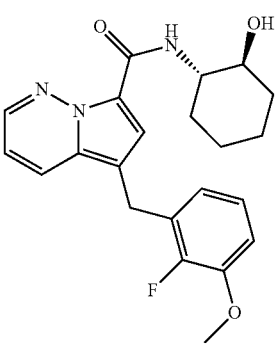 [SMILES: COc1cccc(Cc2cc(C(=O)N[C@H]3CCCC[C@@H]3O)n3ncccc23)c1F]<br>N-(cis-1S,2S-2-Hydroxycyclohexyl)-5-(2-fluoro-3-methoxybenzyl)-pyrrolo[1,2-b]pyridazine-7-carboxamide | $^1$H-NMR (400 MHz, CDCl$_3$): δ 9.02 (d, J = 7.6 Hz, 1H), 8.17 (d, J = 4.0 Hz, 1H), 7.93 (d, J = 12.0 Hz, 1H), 7.55 (s, 1H), 6.98 (t, J = 10.8 Hz, 1H), 6.83-6.68 (m, 3H), 4.11 (s, 2H), 3.94-3.89 (m, 1H), 3.86 (s, 3H), 3.54-3.46 (m, 1H), 2.14-2.06 (m, 2H), 1.78-1.75 (m, 2H), 1.52-1.25 (m, 4H); Mass (m/z): 398.2 (M + H)$^+$. |

-continued

| Ex. No | Chemical Structure | Analytical Characterization |
|---|---|---|
| Example 19 | 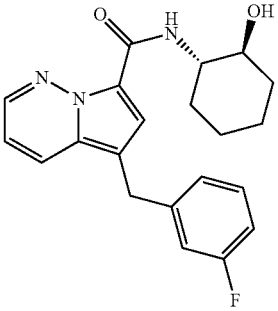 [SMILES: O=C(N[C@H]1CCCC[C@@H]1O)c1cc(Cc2cccc(F)c2)c2cccnn12]<br>N-(cis-1S,2S-2-Hydroxycyclohexyl)-5-(3-fluorobenzyl)-pyrrolo[1,2-b]pyridazine-7-carboxamide | $^1$H-NMR (400 MHz, CDCl$_3$): δ 9.03 (d, J = 8.0 Hz, 1H), 8.19 (d, J = 5.6 Hz, 1H), 7.78 (d, J = 12.4 Hz, 1H), 7.55 (s, 1H), 7.2-7.1 (m, 1H), 6.99 (d, J = 10.4 Hz, 1H), 6.91-6.83 (m, 2H), 6.72 (dd, J = 12.0, 6.0 Hz, 1H), 4.11 (s, 2H), 3.98-3.88 (m, 1H), 3.54-3.47 (m, 1H), 2.15-2.08 (m, 2H), 1.79-1.46 (m, 2H), 1.53-1.26 (m, 4H); Mass (m/z): 368.2 (M + H)$^+$. |
| Example 20 | 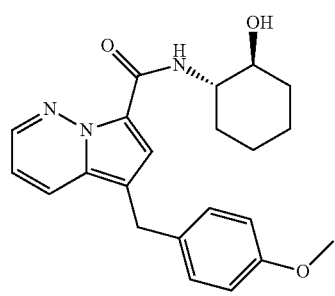 [SMILES: COc1ccc(Cc2cc(C(=O)N[C@H]3CCCC[C@@H]3O)n3ncccc23)cc1]<br>N-(cis-1S,2S-2-Hydroxycyclohexyl)-5-(4-methoxybenzyl)-pyrrolo[1,2-b]pyridazine-7-carboxamide | $^1$H-NMR (400 MHz, CDCl$_3$): δ 9.03 (d, J = 6.1 Hz, 1H), 8.16 (d. J = 4.04, Hz, 1H), 7.76 (d, J = 8.9 Hz, 1H), 7.53 (s, 1H), 7.11 (d, J = 8.3 Hz, 2H), 6.82 (d, J = 8.5 Hz, 2H), 6.67 (dd, J = 9.0 Hz, J = 4.4 Hz, 1H), 4.2 (d, J = 3.2 Hz, 1H), 4.05 (s, 2H), 3.96-3.88 (m, 1H), 3.77 (s, 3H), 3.53-3.47 (m, 1H), 2.14 (m, 2H), 1.78-1.75 (m, 2H), 1.38-1.25 (m, 4H); Mass (m/z): 380.1 (M + H)$^+$. |
| Example 21 | 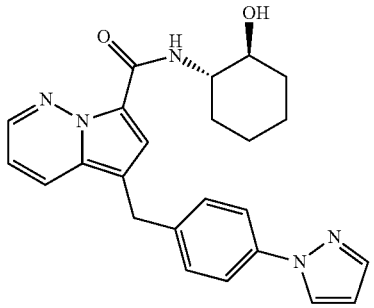 [SMILES: O=C(N[C@H]1CCCC[C@@H]1O)c1cc(Cc2ccc(-n3cccn3)cc2)c2cccnn12]<br>N-(cis-1S,2S-2-Hydroxycyclohexyl)-5-(4-pyrazol-1-ylbenzyl)-pyrrolo[1,2-b]pyridazine-7-carboxamide | $^1$H-NMR (400 MHz, CDCl$_3$): δ 9.03 (d, J = 6.3 Hz, 1H) 8.18 (d, J = 4.3 Hz, 1H), 7.88 (d, J = 2.2 Hz, 1H), 7.76 (d, J = 9.2 Hz, 1H), 7.7 (s, 1H), 7.6-7.58 (m, 3H) 7.29-7.26 (m, 2H), 6.69 (dd, J = 9.1, 4.5, 1H), 6.45 (d, J = 1.6 Hz, 1H), 4.15 (s, 2H), 3.97-3.89 (m, 1H), 3.55-3.48 (m, 1H), 2.14-2.10 (m, 2H), 1.79, 1.76 (m, 2H), 1.48-1.27 (m, 4H); Mass (m/z): 415.9 (M + H)$^+$. |
| Example 22 | 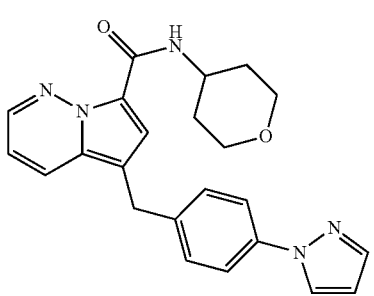 [SMILES: O=C(NC1CCOCC1)c1cc(Cc2ccc(-n3cccn3)cc2)c2cccnn12]<br>N-(Tetrahydropyran-4-yl)-5-(4-pyrazol-1-ylbenzyl)-pyrrolo[1,2-b]pyridazine-7-carboxamide | $^1$H-NMR (400 MHz, CDCl$_3$): δ 9.96 (s, 1H), 8.19 (s, 1H), 7.80 (s, 1H), 7.76-7.71 (m, 2H), 7.61-7.59 (m, 3H), 7.29 (s, 2H), 6.68 (m, 1H), 6.46 (s, 1H), 4.31 (m, 1H), 4.16 (s, 2H), 4.02-4.0 (m, 2H), 3.63-3.57 (m, 2H), 2.08-2.05 (m, 2H), 1.73-1.69 (m, 2H); Mass (m/z): 402.1 (M + H)$^+$. |

| Ex. No | Chemical Structure | Analytical Characterization |
|---|---|---|
| Example 23 | 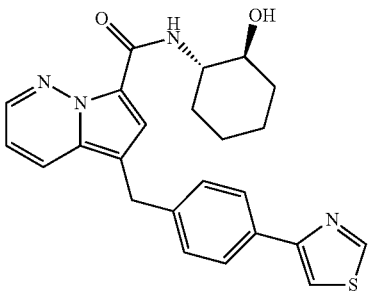 [SMILES: O=C(N[C@H]1CCCC[C@@H]1O)c1cc(Cc2ccc(-c3cscn3)cc2)c2cccnn12]<br>N-(cis-1S,2S-2-Hydroxycyclohexyl)-5-(4-thiazol-4-ylbenzyl)-pyrrolo[1,2-b]pyridazine-7-carboxamide | $^1$H-NMR (400 MHz, CDCl$_3$): δ 9.04 (d, J = 8.0 Hz, 1H), 8.87 (d, J = 2.4 Hz, 1H), 8.17 (d, J = 3.6 Hz, 1H), 7.85 (d, J = 10.8 Hz, 2H), 7.77 (d, J = 12.0 Hz, 1H), 7.59 (s, 1H), 7.49 (d, J = 2.4 Hz, 1H), 7.28 (d, J = 10.8 Hz, 2H), 6.69 (dd, J = 6.0, 12.0 Hz, 1H), 4.16 (s, 2H), 4.02-3.85 (m, 1H), 3.60-3.45 (m, 1H), 2.20-2.05 (m, 2H), 1.83-1.71 (m, 2H), 1.55-1.25 (m, 4H); Mass (m/z): 433.1 (M + H)$^+$. |
| Example 24 | 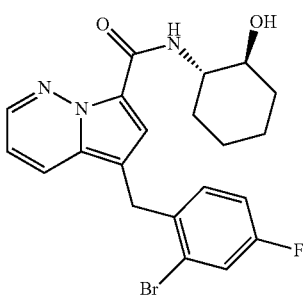 [SMILES: O=C(N[C@H]1CCCC[C@@H]1O)c1cc(Cc2ccc(F)cc2Br)c2cccnn12]<br>N-(cis-1S,2S-2-Hydroxycyclohexyl)-5-(2-bromo-4-fluorobenzyl)-pyrrolo[1,2-b]pyridazine-7-carboxamide | $^1$H-NMR (400 MHz, CDCl$_3$): δ 9.01 (d, J = 8.4 Hz, 1H), 8.19 (d, J = 4.8 Hz, 1H), 7.87 (d, J = 12.0 Hz, 1H), 7.53 (s, 1H), 7.19 (t, J = 14.0 Hz, 2H), 7.04 (t, J = 10.8 Hz, 1H), 6.75 (dd, J = 6.0, 12.0 Hz, 1H), 4.06 (s, 2H), 4.0-3.86 (m, 1H), 3.60-3.45 (m, 1H), 2.20-2.04 (m, 2H), 1.82-1.72 (m, 2H), 1.54-1.23 (m, 4H); Mass (m/z): 446.0, 448.0 (M + H)$^+$. |
| Example 25 | 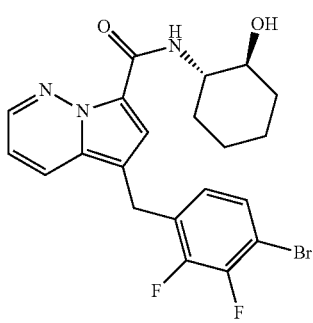 [SMILES: O=C(N[C@H]1CCCC[C@@H]1O)c1cc(Cc2ccc(Br)c(F)c2F)c2cccnn12]<br>N-(cis-1S,2S-2-Hydroxycyclohexyl)-5-(2,3-difluoro-4-bromobenzyl)-pyrrolo[1,2-b]pyridazine-7-carboxamide | $^1$H-NMR (400 MHz, CDCl$_3$): δ 9.00 (d, J = 8.4 Hz, 1H), 8.21 (d, J = 3.6 Hz, 1H), 7.89 (d, J = 12.0 Hz, 1H), 7.53 (s, 1H), 7.22 (t, J = 10.8 Hz, 1H), 6.84 (t, J = 9.2 Hz, 1H), 6.77 (dd, J = 6.0, 12.0 Hz, 1H), 4.10 (s, 2H), 4.05 (bs, 1H), 4.0-3.86 (m, 1H), 3.60-3.45 (m, 1H), 2.20-2.04 (m, 2H), 1.82-1.72 (m, 2H), 1.55-1.25 (m, 4H); Mass (m/z): 464.1, 466.1 (M + H)$^+$. |

| Ex. No | Chemical Structure | Analytical Characterization |
|---|---|---|
| Example 26 | N-(cis-1S,2S-2-Hydroxycyclohexyl)-5-(3-bromo-4-fluorobenzyl)-pyrrolo[1,2-b]pyridazine-7-carboxamide | $^1$H-NMR (400 MHz, CDCl$_3$): δ 9.02 (d, J = 7.2 Hz, 1H), 8.20 (d, J = 4.4 Hz, 1H), 7.76 (d, J = 12.0 Hz, 1H), 7.53 (s, 1H), 7.35 (d, J = 8.0 Hz, 1H), 7.15-7.05 (m, 1H), 7.01 (t, J = 10.8 Hz, 1H), 6.74 (dd, J = 6.0, 12.0 Hz, 1H), 4.11 (bs, 1H), 4.07 (s, 2H), 4.0-3.87 (m, 1H), 3.60-3.48 (m, 1H), 2.20-2.05 (m, 2H), 1.82-1.72 (m, 2H), 1.55-1.21 (m, 4H); Mass (m/z): 446.0, 448.0 (M + H)$^+$. |
| Example 27 | N-(cis-1S,2S-2-Hydroxycyclohexyl)-5-(3-bromobenzyl)-pyrrolo[1,2-b]pyridazine-7-carboxamide | $^1$H-NMR (300 MHz, CDCl$_3$): δ 9.03 (d, J = 8.4 Hz, 1H), 8.19 (d, J = 4.0 Hz, 1H), 7.78 (d, J = 12.0 Hz, 1H), 7.54 (s, 1H), 7.40-7.30 (m, 2H), 7.20-7.10 (m, 2H), 6.73 (dd, J = 6.0, 12.0 Hz, 1H), 4.14 (bs, 1H), 4.08 (s, 2H), 4.0-3.87 (m, 1H), 3.59-3.46 (m, 1H), 2.20-2.05 (m, 2H), 1.82-1.72 (m, 2H), 1.55-1.24 (m, 4H); Mass (m/z): 428.1, 430.1 (M + H)$^+$. |
| Example 28 | N-(cis-1S,2S-2-Hydroxycyclohexyl)-5-(2-chloropyridin-3-ylmethyl)-pyrrolo[1,2-b]pyridazine-7-carboxamide | $^1$H-NMR (300 MHz, CDCl$_3$): δ 9.02 (d, J = 8.4 Hz, 1H), 8.27 (d, J = 4.0 Hz, 1H), 8.22 (d, J = 4.0 Hz, 1H), 7.91 (d, J = 12.0 Hz, 1H), 7.53 (s, 1H), 7.47 (d, J = 10.0 Hz, 1H), 7.17 (dd, J = 6.4, 10.0 Hz, 1H), 6.78 (dd, J = 6.0, 12.0 Hz, 1H), 4.21 (s, 2H), 4.06 (bs, 1H), 4.0-3.88 (m, 1H), 3.59-3.47 (m, 1H), 2.20-2.05 (m, 2H), 1.82-1.72 (m, 2H), 1.55-1.22 (m, 4H); Mass (m/z): 385.0, 387.0 (M + H)$^+$. |

| Ex. No | Chemical Structure | Analytical Characterization |
|---|---|---|
| Example 29 | 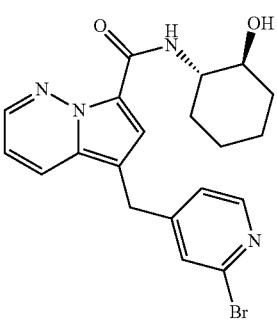 [SMILES: O=C(N[C@H]1CCCC[C@@H]1O)c1cc(Cc2ccnc(Br)c2)c2cccnn12]<br>N-(cis-1S,2S-2-Hydroxycyclohexyl)-5-(2-bromopyridin-4-ylmethyl)-pyrrolo[1,2-b]pyridazine-7-carboxamide | $^1$H-NMR (300 MHz, CDCl$_3$): δ 9.0 (d, J = 8.8 Hz, 1H), 8.25 (d, J = 4.0 Hz, 1H), 8.23 (s, 1H), 7.76 (d, J = 12.0 Hz, 1H), 7.56 (s, 1H), 7.28 (d, J = 10.0 Hz, 1H), 7.07 (d, J = 6.0 Hz, 1H), 6.77 (dd, J = 6.0, 12.0 Hz, 1H), 4.09 (s, 2H), 4.05-3.85 (m, 2H), 3.60-3.48 (m, 1H), 2.20-2.06 (m, 2H), 1.83-1.72 (m, 2H), 1.55-1.22 (m, 4H); Mass (m/z): 429.0, 431.1 (M + H)$^+$. |
| Example 30 | 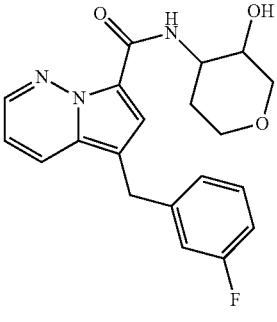 [SMILES: O=C(NC1CCOCC1O)c1cc(Cc2cccc(F)c2)c2cccnn12]<br>N-(3-Hydroxytetrahydropyran-4-yl)-5-(3-fluorobenzyl)-pyrrolo[1,2-b]pyridazine-7-carboxamide | $^1$H-NMR (400 MHz, CDCl$_3$): δ 9.14 (d, J = 5.6 Hz, 1H), 8.21 (d, J = 3.6 Hz, 1H), 7.79 (dd, J = 1.2, 8.8 Hz, 1H), 7.55 (s, 1H), 7.28-7.21 (m, 1H), 6.99 (d, J = 7.6 Hz, 1H), 6.94-6.83 (m, 2H), 6.74 (dd, J = 4.4, 9.2 Hz, 1H), 4.90 (d, J = 2.8 Hz, 1H), 4.11 (s, 2H), 4.10-3.98 (m, 3H), 3.70-3.60 (m, 1H), 3.51 (dt, J = 2.8, 11.6 Hz, 1H), 3.23 (t, J = 10.4 Hz, 1H), 2.08 (dd, J = 2.4, 12.8 Hz, 1H), 1.89 (ddd, J = 4.8, 12.0, 16.8 Hz, 1H); Mass (m/z): 370.2 (M + H)$^+$. |
| Example 31 | 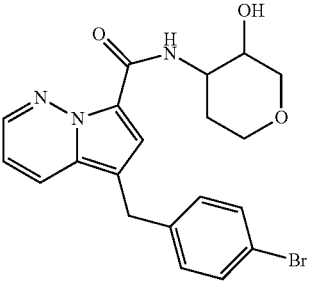 [SMILES: O=C(NC1CCOCC1O)c1cc(Cc2ccc(Br)cc2)c2cccnn12]<br>N-(3-Hydroxytetrahydropyran-4-yl)-5-(4-bromobenzyl)-pyrrolo[1,2-b]pyridazine-7-carboxamide | $^1$H-NMR (400 MHz, CDCl$_3$): δ 9.13 (d, J = 5.6 Hz, 1H), 8.21 (d, J = 3.2 Hz, 1H), 7.77 (dd, J = 1.2, 9.2 Hz, 1H), 7.53 (s, 1H), 7.40 (d J = 8.4 Hz, 2H), 7.07 (d, J = 8.0 Hz, 2H), 6.74 (dd, J = 4.4, 9.2 Hz, 1H), 4.89 (d, J = 2.8 Hz, 1H), 4.13-3.98 (, 5H), 3.70-3.60 (m, 1H), 3.48 (dt, J = 1.6, 11.6 Hz, 1H), 3.23 (t, J = 10.8 Hz, 1H), 2.07 (dd, J = 4.4, 12.8 Hz, 1H), 1.89 (ddd, J = 4.8, 12.0, 16.8 Hz, 1H); Mass (m/z): 430.1, 432.1 (M + H)$^+$. |

Example 32

N-(cis-1S,2S-2-Hydroxycyclohexyl)-5-[4-(1-methyl-1H-pyrazol-4-yl)-benzyl]-pyrrolo [1,2-b]pyridazine-7-carboxamide

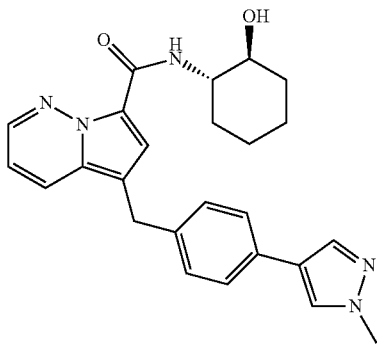 [SMILES: Cn1cc(-c2ccc(Cc3cc(C(=O)N[C@H]4CCCC[C@@H]4O)n4ncccc34)cc2)cn1]

Step 1: Synthesis of ethyl 5-[4-(1-methyl-1H-pyrazol-4-yl)-benzyl]-pyrrolo[1,2-b]pyridazine-7-carboxylate To a stirred solution of ethyl 5-(4-bromobenzyl)-pyrrolo [1,2-b]pyridazine-7-carboxylate, obtained in step 3 of example 1 (1.0 g, 2.78 mmols) in 1,4-dioxane (27.8 mL), $K_2CO_3$ (0.58 g, 4.2 mmols), 1-methylpyrazole-4-boronic acid (0.42 g, 3.3 mmols) and $H_2O$ (5.6 mL) were added in sequence at RT. After degassing for 10 minutes, 1,1'-Bis (diphenylphosphino)ferrocene-palladium(II)dichloride dichloromethane complex (0.22 g, 0.27 mmol) was added. The reaction temperature was raised to 100° C. and stirred for 3 h at this temperature. The reaction mixture was cooled to RT, filtered through celite bed and washed with EtOAc. The combined filtrate was washed with water followed by brine, dried over anhydrous $Na_2SO_4$ and the solvent was removed under reduced pressure to obtain a crude product which was purified by silica gel column chromatography to obtain the title compound.

Yield: 496.0 mg (50%); $^1$H-NMR (400 MHz, $CDCl_3$): δ 8.33 (d, J 3.0 Hz, 1H), 7.73 (s, 1H), 7.73 (d, J=6.0 Hz, 1H), 7.58 (s, 1H), 7.40 (d, J 7.9 Hz, 2H), 7.39 (s, 1H), 7.20 (d, J 7.9 Hz, 2H) 6.73 (dd, J=9.0, 4.36 Hz, 1H), 4.43 (m, 2H), 4.1 (s, 2H), 3.93 (s, 3H), 1.41 (t, 3H); Mass (m/z): 361.1 $(M+H)^+$.

Step 2: Synthesis of 5-[4-(1-methyl-1H-pyrazol-4-yl)-benzyl]-pyrrolo[1,2-b]pyridazine-7-carboxylic acid To a stirred solution of ethyl 5-[4-(1-methyl-1H-pyrazol-4-yl)-benzyl]-pyrrolo[1,2-b]pyridazine-7-carboxylate, obtained in above step (0.49 g, 1.37 mmols) in 2:1 mixture of $H_2O$ and ethanol (6.0 mL), NaOH (0.11 g, 2.75 mmols) was added at 0° C. After stirring for 2 hours at reflux temperature, the reaction mixture was cooled to RT, acidified with 2N HCl and extracted with DCM. The combined organic layer was washed with brine solution, dried over anhydrous $Na_2SO_4$ and the solvent was removed under reduced pressure to obtain the title compound.

Yield: 0.49 g (100%); $^1$H-NMR (400 MHz, $CDCl_3$): δ 12.07 (s, 1H), 8.25 (d, J 3.5 Hz, 1H), 7.85 (d, J 9.2 Hz, 1H), 7.73 (s, 1H), 7.58 (s, 2H), 7.42 (d, J 7.7 Hz, 2H), 7.2 (d, J=7.9 Hz, 2H), 6.82 (dd, J=8.9, 4.4 Hz, 1H), 4.13 (s, 2H), 3.39 (s, 3H); Mass (m/z): 333.1 $(M+H)^+$.

Step 3: Synthesis of N-(cis-1S,2S-2-hydroxycyclohexyl)-5-[4-(1-methyl-1H-pyrazol-4-yl)-benzyl]-pyrrolo[1,2-b]pyridazine-7-carboxamide To a stirred solution of 5-[4-(1-methyl-1H-pyrazol-4-yl)-benzyl]-pyrrolo[1,2-b]pyridazine-7-carboxylic acid, obtained in above step (492 mg, 1.48 mmols) in DCM (6.1 mL), DIPEA (0.7 mL, 3.9 mmol), 1-aminocyclohexanol hydrochloride (225.0 mg, 1.48 mmols) and TBTU (533.0 mg, 1.62 mmol) were added in sequence at 0° C. After stirring for 16 hour at RT, the reaction mixture was diluted with water and DCM. The two layers were separated and aqueous layer was extracted with DCM. The combined organic layer was washed with brine solution, dried over anhydrous $Na_2SO_4$ and the solvent was removed under reduced pressure to obtain a crude product which was purified by silica gel column chromatography to obtain the title compound.

Yield: 457.0 mg (72%); $^1$H-NMR (400 MHz, $CDCl_3$): δ 9.03 (d, J=6.52 Hz, 1H), 8.17 (d, J=4.32 Hz, 1H), 7.79 (d, J=8.96 Hz, 1H), 7.71 (s, 1H), 7.57 (d, j=2.96 Hz, 2H), 7.38 (d, J=8 Hz, 2H), 7.19 (d, J=7.96 Hz, 2H), 6.69 (dd, J=8.96 Hz, 4.4 Hz, 1H), 4.19 (d, J=3.5 Hz, 1H), 4.11 (s, 2H), 3.93 (s, 3H), 3.91-3.89 (m, 1H), 3.55-3.48 (m, 1H), 2.14-2.08 (m, 2H), 1.79-1.76 (m, 2H), 1.51-1.31 (m, 4H); Mass (m/z): 430.3 $(M+H)^m$.

The following Example 33 to Example 40 were prepared by following the experimental procedure as described in Example 32 with some non-critical variations.

| Ex. No | Chemical Structure | Analytical Characterization |
|---|---|---|
| Example 33 | N-(cis-1S,2S-2-Hydroxycyclohexyl)-5-[3-fluoro-4-(1-methyl-1H-pyrazol-4-yl)-benzyl]-pyrrolo[1,2-b]pyridazine-7-carboxamide | $^1$H-NMR (400 MHz, $CDCl_3$): δ 9.03 (d, J = 6.6 Hz, 1H), 8.19 (d, J = 4.3 Hz, 1H), 7.80 (s, 1H), 7.78 (dd, J = 2.0, 8.9 Hz, 1H), 7.72 (d, J = 2.0 Hz, 1H), 7.57 (s, 1H), 7.45 (t, J = 7.9 Hz, 1H), 6.99 (d, J = 7.8 Hz, 1H), 6.92 (d J = 12.0 Hz, 1H), 6.71 (dd, J = 4.4, 9.0 Hz, 1H), 4.14 (d, J = 2.7 Hz, 1H), 4.11 (s, 2H), 3.94 (s, 3H), 3.94-3.89 (m, 1H), 3.54-3.49 (m, 1H), 2.14-2.08 (m, 2H), 1.79-1.76 (m, 2H), 1.49-1.27 (m, 4H); Mass (m/z): 448.2 $(M + H)^+$. |

| Ex. No | Chemical Structure | Analytical Characterization |
|---|---|---|
| Example 34 | 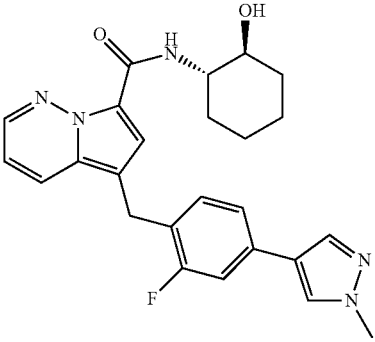 [SMILES: Cn1cc(-c2ccc(Cc3cc(C(=O)N[C@H]4CCCC[C@@H]4O)n4ncccc34)c(F)c2)cn1]<br>N-(cis-1S,2S-2-Hydroxycyclohexyl)-5-[2-fluoro-4-(1-methyl-1H-pyrazol-4-yl)-benzyl]-pyrrolo[1,2-b]pyridazine-7-carboxamide | $^1$H-NMR (400 MHz, CDCl$_3$): δ 9.03 (d, J = 6.4 Hz, 1H), 8.18 (d, J = 3.2 Hz, 1H), 7.92 (d, J = 8.9 Hz, 1H), 7.62 (s, 1H), 7.58 (s, 1H), 7.50 (s, 1H), 7.26-7.21 (m, 2H), 7.04 (t, J = 9.0 Hz, 1H), 6.99 (dd, J = 4.5, 9.1 Hz, 1H), 4.18 (d, J = 3.4 Hz, 1H), 4.12 (s, 2H), 3.95-3.87 (m, 4H), 3.53-3.48 (m, 1H), 2.13-2.06 (m, 2H), 1.78-1.75 (m, 2H), 1.48-1.30 (m, 4H); Mass (m/z): 448.2 (M + H)$^+$. |
| Example 35 | 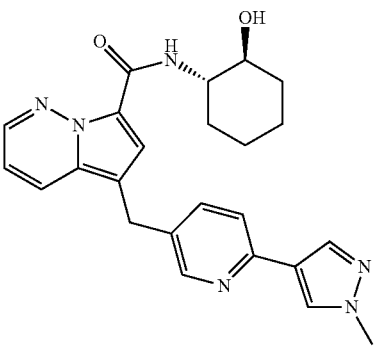<br>N-(cis-1S,2S-2-Hydroxycyclohexyl)-5-[6-(1-methyl-1H-pyrazol-4-yl)-pyridin-3-ylmethyl]-pyrrolo[1,2-b]pyridazine-7-carboxamide | $^1$H-NMR (400 MHz, CDCl$_3$): δ 9.01 (d, J = 6.7 Hz, 1H), 8.45 (s, 1H), 8.2 (d, J = 4.3 Hz, 1H), 7.90 (s, 1H), 7.88 (s, 1H), 7.80 (d, J = 8.8 Hz, 1H), 7.56 (s, 1H), 7.43 (d, J = 2 Hz, 1H), 7.36 (d, J = 8.4 Hz, 1H), 6.72 (dd, J = 8.9, 4.4 Hz, 1H), 4.11 (s, 2H), 3.94-3.92 (m, 5H), 3.54-3.49 (m, 1H), 2.13-2.08 (m, 2H), 1.79-1.76 (m, 2H), 1.52-1.28 (m, 4H); Mass (m/z): 431.3 (M + H)$^+$. |
| Example 36 | 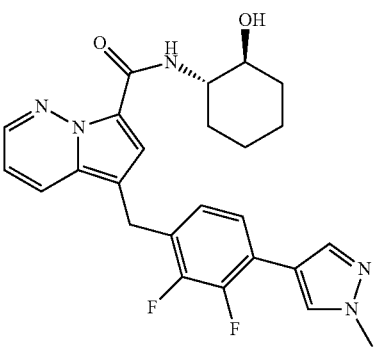 [SMILES: Cn1cc(-c2ccc(Cc3cc(C(=O)N[C@H]4CCCC[C@@H]4O)n4ncccc34)c(F)c2F)cn1]<br>N-(cis-1S,2S-2-Hydroxycyclohexyl)-5-[2,3-difluoro-4-(1-methyl-1H-pyrazol-4-yl)-benzyl]-pyrrolo[1,2-b]pyridazine-7-carboxamide | $^1$H-NMR (300 MHz, CDCl$_3$): δ 9.02 (d, J = 8.8 Hz, 1H), 8.20 (d, J = 4.4 Hz, 1H), 7.92 (d, J = 11.2 Hz, 1H), 7.79 (s, 1H), 7.73 (s, 1H), 7.56 (s, 1H), 7.16 (t, J = 9.6 Hz, 1H), 6.93 (t, J = 10.0 Hz, 1H), 6.76 (dd, J = 6.0, 12.0 Hz, 1H), 4.13 (s, 2H), 3.95 (s, 3H), 3.94-3.85 (m, 1H), 3.60-3.45 (m, 1H), 2.20-2.02 (m, 2H), 1.83-1.72 (m, 2H), 1.52-1.20 (m, 4H); Mass (m/z): 466.1 (M + H)$^+$. |

-continued

| Ex. No | Chemical Structure | Analytical Characterization |
|---|---|---|
| Example 37 | 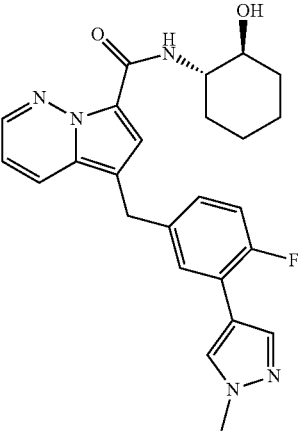 [SMILES: Cn1cc(-c2cc(Cc3cc(C(=O)N[C@H]4CCCC[C@@H]4O)n4ncccc34)ccc2F)cn1]<br>N-(cis-1S,2S-2-Hydroxycyclohexyl)-5-[4-fluoro-3-(1-methyl-1H-pyrazol-4-yl)-benzyl]-pyrrolo[1,2-b]pyridazine-7-carboxamide | $^1$H-NMR (300 MHz, CDCl$_3$): δ 9.04 (d, J = 8.4 Hz, 1H), 8.18 (d, J = 4.4 Hz, 1H), 7.78 (s, 1H), 7.76 (d, J = 11.2 Hz, 1H), 7.73 (s, 1H), 7.55 (s, 1H), 7.35 (d, J = 9.6 Hz, 1H), 7.05-6.95 (m, 2H), 6.71 (dd, J = 6.4, 12.0 Hz, 1H), 4.17 (bs, 1H), 4.10 (s, 2H), 3.94 (s, 3H), 3.94-3.85 (m, 1H), 3.60-3.45 (m, 1H), 2.20-2.02 (m, 2H), 1.83-1.72 (m, 2H), 1.52-1.20 (m, 4H); Mass (m/z): 448.2 (M + H)$^+$. |
| Example 38 | 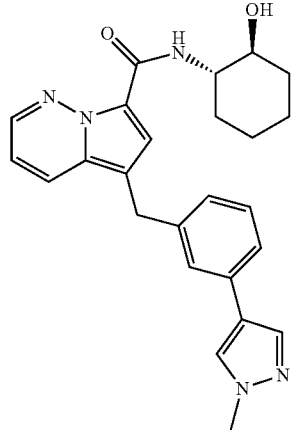 [SMILES: Cn1cc(-c2cccc(Cc3cc(C(=O)N[C@H]4CCCC[C@@H]4O)n4ncccc34)c2)cn1]<br>N-(cis-1S,2S-2-Hydroxycyclohexyl)-5-[3-(1-methyl-1H-pyrazol-4-yl)-benzyl]-pyrrolo[1,2-b]pyridazine-7-carboxamide | $^1$H-NMR (300 MHz, CDCl$_3$): δ 9.05 (d, J = 8.8 Hz, 1H), 8.17 (d, J = 5.2 Hz, 1H), 7.79 (d, J = 12.0 Hz, 1H), 7.70 (s, 1H), 7.58 (s, 1H), 7.56 (s, 1H), 7.35-7.0 (m, 3H), 7.06 (d, J = 9.6 Hz, 1H), 6.69 (dd, J = 6.4, 12.0 Hz, 1H), 4.21 (bs, 1H), 4.12 (s, 2H), 4.0-3.85 (m, 1H), 3.92 (s, 3H), 3.60-3.45 (m, 1H), 2.20-2.05 (m, 2H), 1.83-1.72 (m, 2H), 1.55-1.25 (m, 4H); Mass (m/z): 430.2 (M + H)$^+$. |
| Example 39 | 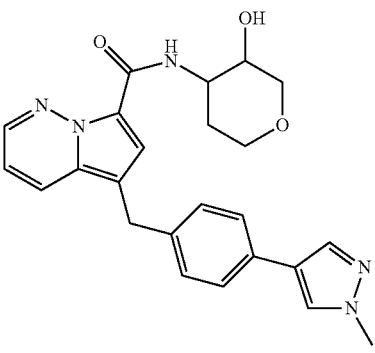 [SMILES: Cn1cc(-c2ccc(Cc3cc(C(=O)NC4CCOCC4O)n4ncccc34)cc2)cn1]<br>N-(3-Hydroxytetrahydropyran-4-yl)-5-[4-(1-methyl-1H-pyrazol-4-yl)-benzyl]-pyrrolo[1,2-b]pyridazine-7-carboxamide | $^1$H-NMR (400 MHz, CDCl$_3$): δ 9.14 (d, J = 5.6 Hz, 1H), 8.20 (d, J = 1.20, 4.0 Hz, 1H), 7.81 (dd, J = 1.6, 9.2 Hz, 1H), 7.71 (s, 1H), 7.57 (s, 1H), 7.56 (s, 1H), 7.38 (d, J = 8.0 Hz, 2H), 7.20 (d, J = 8.0 Hz, 2H), 6.72 (dd, J = 4.8, 9.2 Hz, 1H), 4.92 (d, J = 2.8 Hz, 1H), 4.11 (s, 2H), 4.11-3.98 (m, 3H), 3.93 (s, 3H), 3.68-3.60 (m, 1H), 3.51 (dt, J = 1.6, 11.6 Hz, 1H), 3.23 (t, J = 10.4 Hz, 1H), 2.07 (dd, J = 2.4, 12.8 Hz, 1H), 1.86 (ddd, J = 4.8, 12.0, 16.8 Hz, 1H); Mass (m/z): 432.2 (M + H)$^+$. |

| Ex. No | Chemical Structure | Analytical Characterization |
|---|---|---|
| Example 40 | 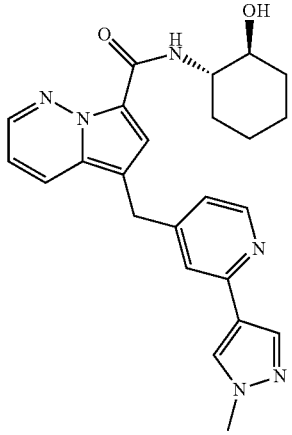 [SMILES: Cn1cc(-c2cc(Cc3cc(C(=O)N[C@H]4CCCC[C@@H]4O)n4ncccc34)ccn2)cn1]<br>N-(cis-1S,2S-2-Hydroxycyclohexyl)-5-[2-(1-methyl-1H-pyrazol-4-yl)-pyridin-4-ylmethyl]-pyrrolo[1,2-b]pyridazine-7-carboxamide | $^1$H-NMR (400 MHz, CDCl$_3$): δ 8.99 (d, J = 8.0 Hz, 1H), 8.45 (d, J = 5.2 Hz, 1H), 8.25 (d, J = 4.0 Hz, 1H), 7.92 (s, 1H), 7.76 (d, J = 8.4 Hz, 1H), 7.61 (s, 1H), 7.45-7.38 (m, 1H), 7.30-7.25 (m, 2H), 7.13-7.05 (m, 1H), 6.78 (dd, J = 4.4, 8.8 Hz, 1H), 4.22 (s, 2H), 3.96 (s, 3H), 3.96-3.88 (m, 2H), 3.60-3.48 (m, 1H), 2.18-2.08 (m, 2H), 1.83-1.75 (m, 2H), 1.55-1.25 (m, 4H); Mass (m/z): 431.2 (M + H)$^+$. |
Example 41
N-(cis-1S,2S-2-Hydroxycyclohexyl)-3-(4-bromobenzyl)-8-fluoroindolizine-1-carboxamide
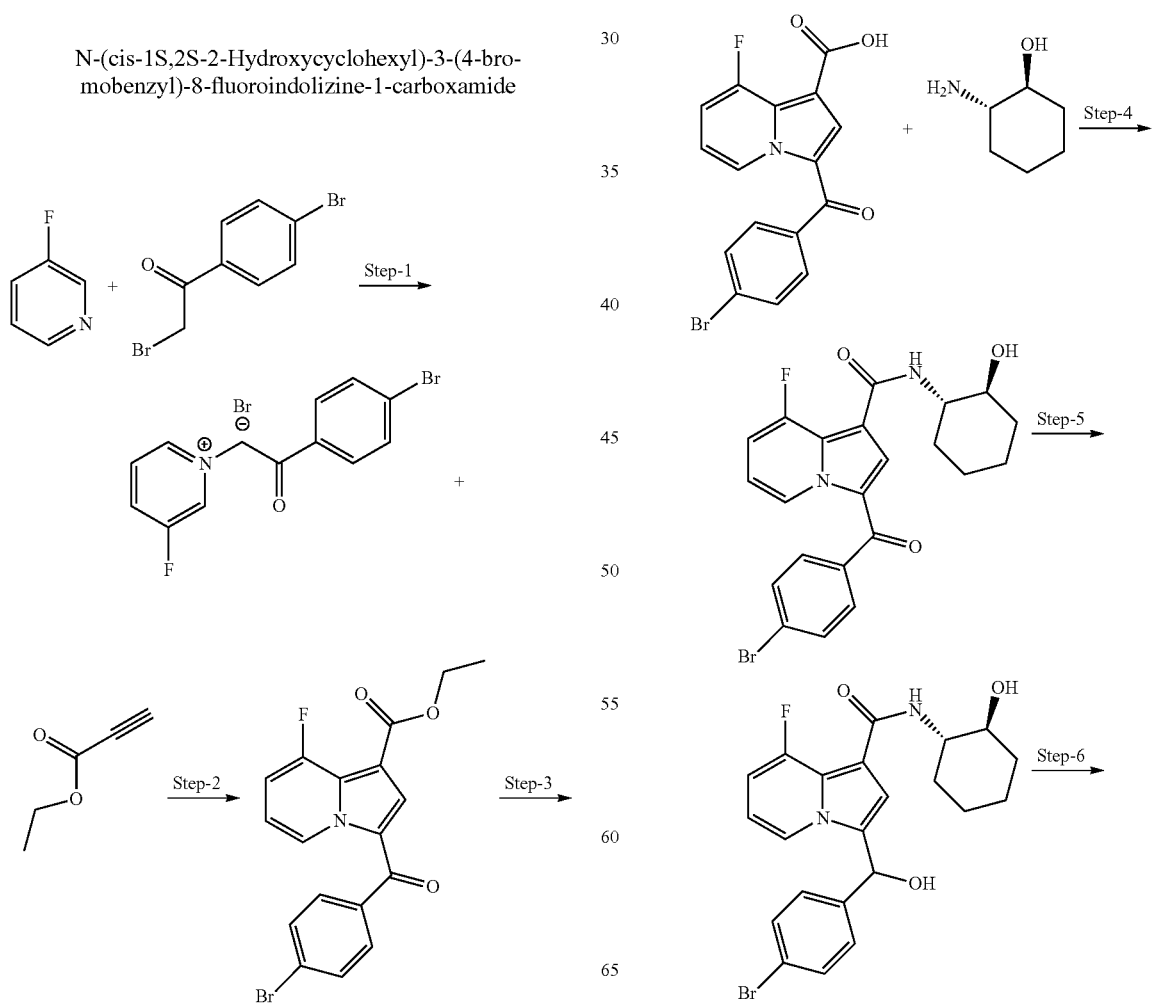

-continued

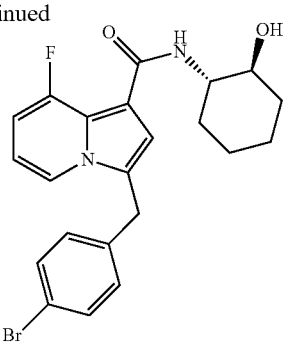

Step 1: Synthesis of 1-[2-(4-bromophenyl)-2-oxo-ethyl]-3-fluoropyridinium bromide To a stirred solution of 3-fluoropyridine (0.8 g, 8.2 mmols) in EtOAc (49.2 mL) cooled at 0° C., 4-bromophenacyl bromide (2.26 g, 8.2 mmols) was added. After stirring for 16 hours at RT, the solids precipitated was filtered, washed with solvent ether, dried under reduced pressure to obtain the title compound.

Yield: 0.85 g (35%); $^1$H-NMR (300 MHz, DMSO): δ 9.36 (s, 1H), 8.96 (d, J=7.8 Hz, 1H), 8.80 (m, 1H), 8.43 (m, 1H), 8.02 (d, J=8.7 Hz, 2H), 7.93 (d, J=8.7 Hz, 2H), 6.49 (s, 2H); Mass (m/z): 294.1, 395.9 (M+H)$^+$.

Step 2: Synthesis of ethyl 3-(4-bromobenzoyl)-8-fluoroindolizine-1-carboxylate To a stirred solution of 1-[2-(4-bromophenyl)-2-oxo-ethyl]-3-fluoropyridinium bromide obtained in step 1 (0.85 g, 2.8 mmols) in dry THF (11.5 mL) at RT, K$_2$CO$_3$ (0.58 g, 4.2 mmols) and ethyl propiolate (0.31 mL, 3.1 mmols) was added. After stirring for 16 hours at RT, the reaction mixture was diluted with water and EtOAc. The two layers were separated and aqueous layer was extracted with EtOAc. The combined organic layer was washed once with brine solution, dried over anhydrous Na$_2$SO$_4$ and the solvent was removed under reduced pressure to obtain a crude product which was purified by silica gel column chromatography to obtain the title compound.

Yield: 0.38 g (35%); $^1$H-NMR (300 MHz, CDCl$_3$): δ 9.8 (d, J=6.9 Hz, 1H), 7.80 (s, 1H), 7.73-7.65 (m, 4H), 7.20-7.11 (m, 1H); 7.08-7.0 (m, 1H), 4.4 (q, 2H), 1.4 (t, J=6.9 Hz, 3H); Mass (m/z): 390.0, 391.9 (M+H)$^+$.

Step 3: Synthesis of 3-(4-bromobenzoyl)-8-fluoroindolizine-1-carboxylic acid To a stirred solution of ethyl 3-(4-bromobenzoyl)-8-fluoroindolizine-1-carboxylate obtained in step 2 (0.2 g, 0.51 mmol) in 1:1 mixture of H$_2$O and methanol (5.0 mL) cooled at 0° C., NaOH (0.041 g, 1.02 mmol) was added. After stirring for 2 hours at reflux temperature, the reaction mixture was cooled to RT, acidified with 2N HCl and extracted with EtOAc. The combined organic layer was washed once with brine solution, dried over anhydrous Na$_2$SO$_4$ and the solvent was removed under reduced pressure to obtain the title compound.

Yield: 0.19 g (100%); $^1$H-NMR (300 MHz, DMSO): δ 12.5 (bs, 1H) 9.7 (d, J=6.9 Hz, 1H), 7.82 (d, J=8.1, 2H), 7.76 (d, J=8.1, 2H) 7.65 (s, 1H), 7.55-7.45 (m, 1H), 7.36-7.25 (m, 1H); Mass (m/z): 360.0, 362.0 (M+H)$^+$.

Step 4: Synthesis of N-(cis-1S,2S-2-hydroxycyclohexyl)-3-(4-bromobenzoyl)-8-fluoroindolizine-1-carboxamide To a stirred solution of 3-(4-bromobenzoyl)-8-fluoroindolizine-1-carboxylic acid obtained in step 3 (175 mg, 0.48 mmol) in DCM (4.8 mL) cooled at 0° C., DIPEA (0.12 mL, 0.72 mmol), 1-aminocyclohexanol hydrochloride (55.0 mg, 0.48 mmol) and HATU (183.0 mg, 0.48 mmol) in sequence were added. After stirring for 16 hour at RT, the reaction mixture was diluted with water and DCM. The two layers were separated and aqueous layer was extracted with DCM. The combined organic layer was washed once with brine solution, dried over anhydrous Na$_2$SO$_4$ and the solvent was removed under reduced pressure to obtain a crude product which was purified by silica gel column chromatography to obtain the title compound.

Yield: 180.0 mg (85%); $^1$H-NMR (300 MHz, CDCl$_3$): δ 9.84 (d, J=6.9 Hz, 1H), 7.89 (s, 1H), 7.71 (d, J=8.4 Hz, 2H), 7.67 (d, J=8.4 Hz, 2H), 7.18-7.10 (m, 1H), 7.05-6.95 (m, 1H), 6.58 (bs, 1H), 3.92-3.82 (m, 1H), 3.50-3.40 (m, 1H), 2.18-2.02 (m, 2H), 1.82-1.70 (m, 2H), 1.52-1.25 (m, 4H); Mass (m/z): 459.0, 461.0 (M+H)$^+$.

Step 5: Synthesis of N-(cis-1S,2S-2-hydroxycyclohexyl)-3-[(4 bromophenyl)hydroxymethyl]-8-fluoroindolizine-1-carboxamide To a stirred solution of N-(cis-1S, 2S-2-hydroxycyclohexyl)-3-(4-bromobenzoyl)-8-fluoroindolizine-1-carboxamide obtained in step 4 (175.0 mg, 0.38 mmols) in methanol (7.6 mL) cooled at 0° C., NaBH$_4$ (21.0 mg, 0.57 mmols) was added. After stirring for 2 hours at RT, the reaction mixture was diluted with water and EtOAc. The two layers were separated and aqueous layer was extracted with EtOAc. The combined organic layer was washed once with brine solution, dried over anhydrous Na$_2$SO$_4$ and the solvent was removed under reduced pressure to obtain the title compound.

Yield: 175.0 mg (100%); $^1$H-NMR (300 MHz, CDCl$_3$): δ 8.07 (d, J=6.9 Hz, 1H), 7.47-7.32 (m, 5H), 7.06 (bs, 1H), 6.78-6.67 (m, 1H), 6.63-6.53 (m, 2H), 6.13 (s, 1H), 4.38 (bs, 1H), 3.88-3.75 (m, 1H), 3.47-3.35 (m, 1H), 2.15-2.0 (m, 2H), 1.70-1.60 (m, 2H), 1.45-1.18 (m, 4H); Mass (m/z): 461.1, 463.1 (M+H)$^+$.

Step 6: Synthesis of N-(cis-1S,2S-2-hydroxycyclohexyl)-3-(4-bromobenzyl)-8-fluoroindolizine-1-carboxamide To a stirred solution of N-(cis-1S,2S-2-hydroxycyclohexyl)-3-[(4-bromophenyl)hydroxymethyl]-8-fluoroindolizine-1-carboxamide obtained in step 5 (170.0 mg, 0.36 mmol) in trifluoroacetic acid (0.29 mL, 3.6 mmols) cooled at −10° C., triethylsilane (0.12 mL, 0.79 mmol) was added. After stirring for 1 hour at 0° C., the reaction mixture was diluted with 10% aq. NaHCO$_3$ solution and EtOAc. The two layers were separated and aqueous layer was extracted with CHCl$_3$. The combined organic layer was washed once with brine solution, dried over anhydrous Na$_2$SO$_4$ and the solvent was removed under reduced pressure to obtain a crude product which was purified by silica gel column chromatography to obtain the title compound.

Yield: 0.9 g (54%); ¹H-NMR (300 MHz, CDCl₃): δ 7.51 (d, J=7.2 Hz, 1H), 7.43 (d, J=8.1 Hz, 2H), 7.23 (s, 1H), 7.03 (d, J=8.1 Hz, 2H), 6.74-6.52 (i, 3H), 4.16 (s, 2H), 3.91-3.80 (i, 1H), 3.50-3.40 (m, 1H), 2.18-2.02 (m, 2H), 1.82-1.72 (i, 2H), 1.45-1.25 (i, 4H); Mass (m/z): 445.1, 447.1 (M+H)⁺.

The following Example 42 to Example 47 were prepared using the experimental procedure as described in the Example 41 with some non-critical variations.

| Ex. No | Chemical Structure | Analytical Characterization |
|---|---|---|
| Example 42 | N-(cis-1S,2S-2-Hydroxycyclohexyl)-3-benzyl-8-fluoroindolizine-1-carboxamide | ¹H-NMR (300 MHz, CDCl₃): δ 7.57 (d, J = 6.6 Hz, 1H), 7.50-7.10 (m, 6H), 6.80-6.65 (m, 2H), 6.60-6.50 (m, 1H), 4.86 (bs, 2H), 4.20 (s, 2H), 3.90-3.80 (m, 1H), 3.55-3.45 (m, 1H), 2.20-2.02 (m, 1H), 1.82-1.70 (m, 2H), 1.50-1.20 (m, 4H); Mass (m/z): 367.3 (M + H)⁺. |
| Example 43 | N-(cis-1S,2S-2-Hydroxycyclohexyl)-3-(2-chloropyridine-4-ylmethyl)-8-fluoroindolizine-1-carboxamide | ¹H-NMR (300 MHz, DMSO): δ 8.33 (d, J = 4.5 Hz, 1H), 7.98 (d, J = 6.3 Hz, 1H), 7.62 (d, J = 6.2 Hz, 1H), 7.40 (s, 1H), 7.26 (d, J = 3.3 Hz, 1H), 7.03 (s, 1H), 6.75-6.71 (m, 2H), 4.62 (d, J = 4.5 Hz, 1H), 4.37 (s, 2H), 3.60 (bs, 1H), 3.14 (m, 1H), 1.89 (m, 2H), 1.61 (m, 2H), 1.23 (m, 4H); Mass (m/z): 402 (M + H)⁺. |
| Example 44 | N-(cis-1S,2S-2-Hydroxycyclohexyl)-3-(4-methoxybenzyl)-8-fluoroindolizine-1-carboxamide | ¹H-NMR (300 MHz, DMSO): δ 7.91 (d, J = 6.6 Hz, 1H), 7.57 (d, J = 6.6 Hz, 1H), 7.18 (d, J = 8.4 Hz, 2H), 6.92 (s, 1H), 6.88 (d, J = 8.7 Hz, 2H), 6.77 (d, J = 6.9 Hz, 1H), 6.7-6.66 (t, J = 6.0 Hz, 1H), 4.63 (d, J = 4.8 Hz, 1H), 4.19 (s, 2H), 3.71 (s, 3H), 3.57 (bs, 1H), 3.16 (m, 1H), 2.68-2.63 (m, 2H), 2.0-1.89 (m, 2H), 1.70-1.64 (m, 2H), 1.35-1.20 (m, 2H); Mass (m/z): 397.0 (M + H)⁺. |

-continued

| Ex. No | Chemical Structure | Analytical Characterization |
|---|---|---|
| Example 45 | 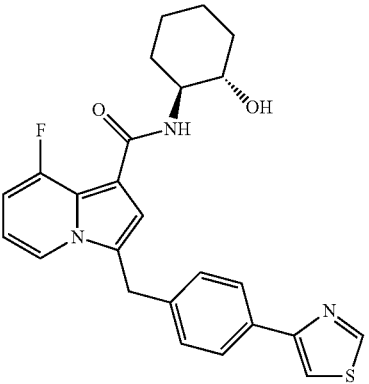 [SMILES: O=C(N[C@H]1CCCC[C@@H]1O)c1cc(Cc2ccc(-c3cscn3)cc2)n2cccc(F)c12]<br>N-(cis-1S,2S-2-Hydroxycyclohexyl)-3-(4-thiazol-4-yl-benzyl)-8-fluoroindolizine-1-carboxamide | $^1$H-NMR (300 MHz, CDCl$_3$): δ 8.8 (s, 1H), 8.43-8.37 (m, 1H), 8.16 (s, 1H), 7.92 (d, J = 8.1 Hz, 2H), 7.76 (d, J = 8.1 Hz, 1H), 7.59 (s, 1H), 7.28 (d, J = 8.1 Hz, 2H), 6.95-6.91 (t, J = 8.4 Hz, 1H), 6.69 (s, 1H), 5.76 (d, J = 5.4 Hz, 1H), 4.21 (s, 2H), 3.51-3.40 (m, 1H), 3.18 (bs, 1H), 2.1-2.03 (m, 2H), 1.77-1.71 (m, 2H), 1.43 1.25 (m, 4H); Mass (m/z): 450 (M + H)$^+$. |
| Example 46 | 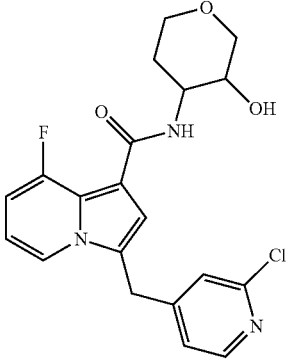 [SMILES: O=C(NC1CCOCC1O)c1cc(Cc2ccnc(Cl)c2)n2cccc(F)c12]<br>N-(3-Hydroxytetrahydropyran-4-yl)-3-(2-chloropyridine-4-ylmethyl)-8-fluoroindolizine-1-carboxamide | $^1$H-NMR (400 MHz, CDCl$_3$): δ 8.34 (d, J = 4.8 1H), 7.98 (d, J = 6.8 Hz, 1H), 7.80 (d, J = 7.2 Hz, 1H), 7.405 (s, 1H), 7.26 (d, J = 5.2 Hz, 1H), 7.03 (s, 1H), 6.81 (t, J = 7.6 Hz, 1H), 6.68 (d, J = 8.4 Hz, 1H), 4.96 (d, J = 5.2 Hz, 1H), 4.37 (s, 2H), 3.85 (s, 2H), 3.81 (t, J = 10.4 Hz, 2H), 3.45-3.40 (m, 1H), 3.06 (t, J = 10.4 Hz, 2H); Mass (m/z): 403.0 (M + H)$^+$. |
| Example 47 | 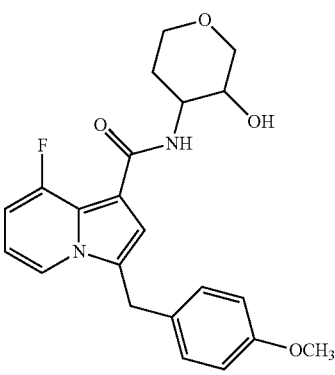 [SMILES: COc1ccc(Cc2cc(C(=O)NC3CCOCC3O)c3c(F)cccn23)cc1]<br>N-(3-Hydroxytetrahydropyran-4-yl)-3-(4-methoxybenzyl)-8-fluoroindolizine-1-carboxamide | $^1$H-NMR (400 MHz, CDCl$_3$): δ 7.59 (d, J = 6.8 Hz, 1H), 7.21 (s, 1H), 7.08 (d, J = 8.4 Hz, 2H), 6.84 (d, J = 8.8 Hz, 2H), 6.72 (d, J = 4.0 Hz, 1H), 6.66 (d, J = 8.4 Hz, 1H), 6.57-6.54 (m, 1H), 4.89 (d, J = 4.2 Hz, 1H), 4.14 (s, 2H), 4.10-3.98 (m, 3H), 3.78 (s, 3H), 3.71-3.70 (m, 1H), 3.52-3.45 (m, 1H), 3.28-3.20 (m, 1H), 2.10-2.05 (m, 1H), 1.90-1.78 (m, 1H); Mass (m/z): 399.0 (M + H)$^+$. |

Example 48

N-(cis-1S,2S-2-Hydroxycyclohexyl)-5-[4-(1-methyl-1H-pyrazol-4-yl)-benzyl]-8-fluoroindolizine-1-carboxamide

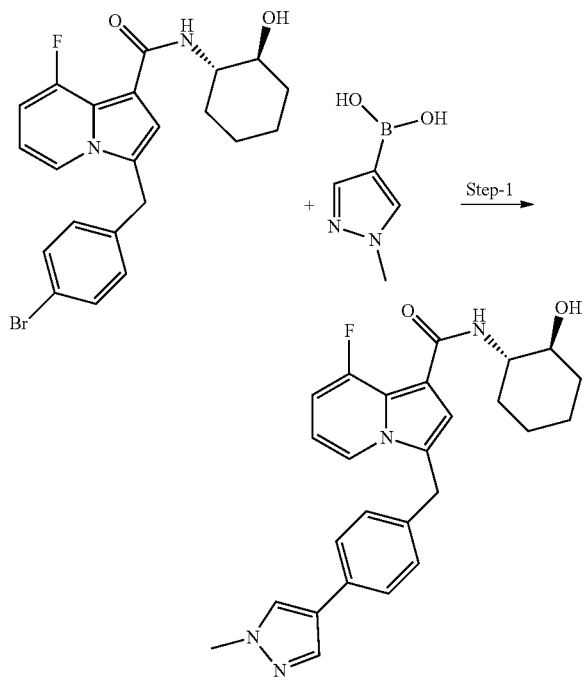

To a stirred solution of N-(cis-1S, 2S-2-hydroxycyclohexyl)-3-(4-bromobenzyl)-8-fluoroindolizine-1-carboxamide obtained in step 6 of example 41 (30.0 mg, 0.06 mmol) in 1,4-dioxane (3.0 mL) at RT, $Na_2CO_3$ (0.019 g, 0.18 mmol), 1-methylpyrazole-4-boronic acid (0.008 g, 0.06 mmol) and $H_2O$ (0.61 mL) in sequence were added. After degassing for 10 minutes, 1,1'-bis(diphenylphosphino)ferrocene-palladium(II)dichloride dichloromethane complex (0.003 g, 0.003 mmol) was added. The reaction temperature was raised to 100° C. and stirred for 3 h at this temperature. After cooling the reaction mixture to RT, it was filtered through celite bed. EtOAc was used in washing the bed. The combined filtrate was washed with water followed by brine, dried over anhydrous $Na_2SO_4$ and the solvent was removed under reduced pressure to obtain a crude product which was purified by silica gel column chromatography to obtain the title compound.

Yield: 8.2 mg (26%); $^1$H-NMR (300 MHz, $CDCl_3$): δ 7.72 (s, 1H), 7.57 (d, J=7.2 Hz, 1H), 7.42 (s, 1H), 7.40 (d, J=8.1 Hz, 2H), 7.23 (s, 1H), 7.15 (d, J=8.1 Hz, 2H), 6.74-6.52 (m, 3H), 4.20 (s, 2H), 3.93 (s, 3H), 3.80-3.70 (m, 1H), 3.50-3.40 (m, 1H), 2.18-2.02 (m, 2H), 1.82-1.72 (m, 2H), 1.45-1.25 (m, 4H); Mass (m/z): 447.3 (M+H)$^+$.

The following Example 49 to Example 51 were prepared using the experimental procedure as descried in the Example 48 with some non-critical variations.

| Ex. No | Chemical Structure | Analytical Characterization |
|---|---|---|
| Example 49 | N-(3-Hydroxytetrahydropyran-4-yl)-3-(4-(1-methyl-1H-pyrazol-4-yl)-benzyl)-8-fluoroindolizine-1-carboxamide | $^1$H-NMR (400 MHz, $CDCl_3$): δ 8.4-8.37 (m, 1H), 7.7 (s, 1H), 7.5-7.64 (m, 1H), 7.6 (s, 1H), 7.4 (d, J = 8.2 Hz, 2H), 7.17 (d, J = 11.6 Hz, 2H), 6.99-6.92 (m, 1H), 6.7 (s, 1H), 5.80 (d, J = 5.6 Hz, 1H), 4.15 (s, 2H), 4.10-4.06 (m, 1H), 4.0-3.90 (m, 2H), 3.70-3.60 (m, 1H), 3.52-3.45 (m, 1H), 3.28-3.19 (m, 1H), 2.10-2.02 (m, 1H), 1.90-1.78 (m, 1H); Mass (m/z); 449.0 (M + H)$^+$. |

| Ex. No | Chemical Structure | Analytical Characterization |
|---|---|---|
| Example 50 | 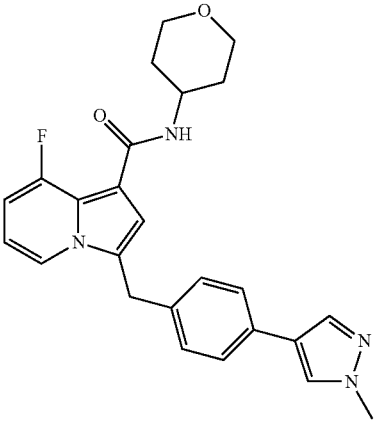 [SMILES: Cn1cc(-c2ccc(Cc3cc(C(=O)NC4CCOCC4)c4c(F)cccn34)cc2)cn1]<br>N-(Tetrahydropyran-4-yl)-3-(4(1-methyl-1H-pyrazol-4-yl)-benzyl)-8-fluoroindolizine-1-carboxamide | $^1$H-NMR (400 MHz, DMSO): δ 8.29 (s, 2H), 8.08 (s, 1H), 7.82-7.78 (t, J = 7.6 Hz, 2H), 7.52 (d, J = 7.2 Hz, 2H), 7.25 (d, J = 7.2 Hz, 2H), 7.06 (s, 1H), 7.06 (t, J = 8.4 Hz, 1H), 4.20-4.12 (m, 1H), 4.19 (s, 2H), 4.05-3.98 (m, 2H), 3.85 (s, 3H), 3.60-3.50 (m, 2H), 2.03-1.95 (m, 2H), 1.72-1.55 (m, 2H); Mass (m/z): 433.0 (M + H)$^+$. |
| Example 51 | 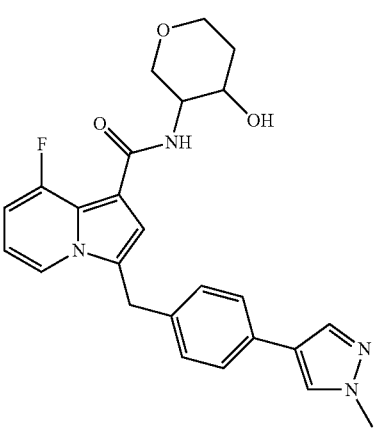 [SMILES: Cn1cc(-c2ccc(Cc3cc(C(=O)NC4COCCC4O)c4c(F)cccn34)cc2)cn1]<br>N-(4-Hydroxytetrahydropyran-3-yl)-3-(4-(1-methyl-1H-pyrazol-4-yl)-benzyl)-8-fluoroindolizine-1-carboxamide | $^1$H-NMR (400 MHz, DMSO-d$_6$): δ 8.31-8.25 (m, 2H), 8.08 (s, 1H), 7.81 (s, 1H), 7.51 (d, J = 8.0 Hz, 2H), 7.25 (d, J = 8.0 Hz, 2H), 7.20 (s, 1H), 7.06 (s, 1H), 5.12 (bs, 1H), 4.21 (s, 2H), 4.10-3.92 (m, 3H), 3.84 (s, 3H), 3.56-3.50 (m, 4H), 1.76-1.72 (m, 2H; Mass (m/z): 449.0 (M + H)$^+$. |

Example 52

Determination of Allosteric Potency EC$_{50}$ Values for Muscarinic M1 Receptor:

A stable CHO cell line expressing recombinant human Muscarinic M1 receptor and pCRE-Luc reporter system was used for cell-based assay. The assay offers a non-radioactive based approach to determine binding of a compound to GPCRs. In this specific assay, the level of intracellular cyclic AMP which is modulated by activation or inhibition of the receptor is measured. The recombinant cells harbor luciferase reporter gene under the control of cAMP response element.

The above cells were grown in 96 well clear bottom white plates in Hams F12 medium containing 10% fetal bovine serum (FBS). Prior to the addition of compounds or standard agonist, cells were serum starved overnight. Increasing concentrations of test compounds were added along with EC$_{20}$ of acetylcholine in OptiMEM medium to the cells. The incubation was continued at 37° C. in CO$_2$ incubator for 4 hours. Medium was removed and cells were washed with phosphate buffered saline. The cells were lysed and luciferase activity was measured in a Luminometer. Luminescence counts in each concentrations of test item were normalized to the acetylcholine induced maximum response and the data was analyzed using Graphpad software. EC$_{50}$ values of the compounds were defined as the concentration required in stimulating the luciferase activity by 50% in presence of EC$_{20}$ of acetylcholine.

| Example No. | EC$_{50}$ (nM) |
|---|---|
| 1 | 1466 |
| 2 | 419 |
| 3 | 653 |
| 4 | 836 |
| 5 | 2132 |
| 6 | 3027 |
| 7 | 779 |
| 8 | 863 |
| 9 | 2112 |
| 10 | 1224 |
| 11 | 1301 |

-continued

| Example No. | EC$_{50}$ (nM) |
|---|---|
| 12 | 1338 |
| 13 | 1762 |
| 14 | 1083 |
| 15 | 1509 |
| 16 | 2765 |
| 17 | 10000 |
| 18 | 3715 |
| 19 | 2104 |
| 20 | 1338 |
| 21 | 179 |
| 22 | 1760 |
| 23 | 119 |
| 24 | 1183 |
| 25 | 2286 |
| 26 | 643 |
| 27 | 1701 |
| 28 | 10000 |
| 29 | 1014 |
| 30 | 1645 |
| 31 | 1034 |
| 32 | 66 |
| 33 | 259 |
| 34 | 989 |
| 35 | 599 |
| 36 | 94 |
| 37 | 1003 |
| 38 | 1528 |
| 39 | 291 |
| 40 | 1654 |
| 41 | 236 |
| 42 | 1129 |
| 43 | 2064 |
| 44 | 1595 |
| 45 | 3193 |
| 46 | 463 |
| 47 | 1106 |
| 48 | 166 |

-continued

| Example No. | EC$_{50}$ (nM) |
|---|---|
| 49 | 1211 |
| 50 | 2528 |
| 51 | 3652 |

Example 53

Rodent Pharmacokinetic Study

Male Wistar rats (260±50 grams) were used as experimental animals. Animals were housed individually in polypropylene cage. Two days prior to study, male Wistar rats were anesthetized with isoflurane for surgical placement of jugular vein catheter. Rats were randomly divided for oral (3 mg/kg) and intravenous (i.v) (1 mg/kg) dosing (n=3/group) and fasted overnight before oral dosing (p.o.). However, rats allocated to intravenous (i.v.) dosing food and water was provided ad libitum.

At pre-determined point, blood was collected through jugular vein and replenished with an equivalent volume of normal saline. Collected blood was transferred into a labeled eppendorf tube containing 10 μL of heparin as an anticoagulant. Typically blood samples were collected at following time points: 0.08, 0.25, 0.5, 1, 2, 4, 6, 8, and 24 hours post dose. Blood was centrifuged at 4000 rpm for 10 minutes. Plasma was separated and stored frozen at −80° C. until analysis. The concentrations of the test compounds were quantified in plasma by qualified LC-MS/MS method using suitable extraction technique. The test compounds were quantified in the calibration range around 1-1000 ng/mL in plasma. Study samples were analyzed using calibration samples in the batch and quality control samples spread across the batch.

Pharmacokinetic parameters Cmax, AUC$_t$, T$_{1/2}$, clearance and bioavailability (F) were calculated by non-compartmental model using standard non-compartmental model by using Phoenix WinNonlin 6.0.2 or 6.0.3 version Software package.

| Example No | ROA | C$_{max}$ (ng/mL) | AUC$_{0-t}$ (ng · hr/mL) | T$_{1/2}$ (hr) | Clearance (mL/min/kg) | F % |
|---|---|---|---|---|---|---|
| 3 | oral | 132 ± 31 | 1390 ± 780 | 3.6 ± 0.2 | — | 49 ± 27 |
|   | i.v. | — | 951 ± 213 | 3.5 ± 1.1 | 17 ± 3 |   |
| 4 | oral | 105 ± 3 | 457 ± 73 | 3.9 ± 1.4 | — | 25 ± 4 |
|   | i.v. | — | 599 ± 58 | 2.4 ± 0.9 | 27 ± 3.4 |   |
| 20 | oral | 402 ± 98 | 1610 ± 139 | 3.4 ± 0.7 | — | 39 ± 3 |
|   | i.v | — | 1380 ± 390 | 2.7 ± 0.8 | 12.2 ± 3.1 |   |
| 21 | oral | 687 ± 169 | 5470 ± 1366 | 3.4 ± 1.01 | — | 49 ± 12 |
|   | i.v. | — | 3703 ± 768 | 2.5 ± 0.7 | 4.6 ± 0.9 |   |
| 32 | oral | 650 ± 224 | 4900 ± 1640 | 3.2 ± 0.4 | — | 50 ± 17 |
|   | i.v. | — | 3257 ± 802 | 3.2 ± 1.2 | 5.2 ± 1.4 |   |
| 33 | oral | 414 ± 21 | 2820 ± 20 | 2.7 ± 0.1 | — | 103 ± 0.7 |
|   | i.v. | — | 908 ± 164 | 1.3 ± 0.2 | 19 ± 3.8 |   |
| 34 | oral | 793 ± 86 | 6393 ± 312 | 4.4 ± 2.3 | — | 66 ± 3 |
|   | i.v. | — | 3227 ± 625 | 3.7 ± 0.3 | 5.0 ± 0.7 |   |

Example 54

Rodent Brain Penetration Study

Male Wistar rats (260±40 grams) were used as experimental animals. Three animals were housed in each cage. Animals were given water and food ad libitum throughout the experiment and maintained on a 12 hours light/dark cycle.

Brain penetration was determined in discrete manner in rats. One day prior to dosing day, male Wistar rats were acclimatized and randomly grouped according to their weight. At each time point (0.5, 1 and 2 hours) n=3 animals were used.

The test compounds were suitably preformulated and administered orally at (free base equivalent) 3 mg/kg. Blood samples were removed via cardiac puncture by using isoflurane anesthesia. The animals were sacrificed to collect brain tissue. Plasma was separated and brain samples were homogenized and stored frozen at −20° C. until analysis. The concentrations of the test compounds in plasma and brain were determined using LC-MS/MS method.

The test compounds were quantified in plasma and brain homogenate by qualified LC-MS/MS method using suitable extraction technique. The test compounds were quantified in the calibration range of 1-500 ng/mL in plasma and brain homogenate. Study samples were analyzed using calibration samples in the batch and quality control samples spread across the batch. Extent of brain-plasma ratio was calculated (Cb/Cp) and the results are tabulated below.

| Example No. | Single dose Rat Brain Penetration (Cb/Cp) at 3 mg/kg, p.o. @ 1.0 hr |
|---|---|
| 3 | 1.90 ± 0.27 |
| 4 | 1.31 ± 0.11 |
| 20 | 1.52 ± 0.15 |
| 21 | 0.24 ± 0.02 |
| 32 | 0.15 ± 0.02 |
| 33 | 0.20 ± 0.001 |
| 34 | 0.13 ± 0.02 |

Example 55

Object Recognition Task Model

The cognition enhancing properties of compounds of this invention were estimated by using this model.

Male Wistar rats (8-10 weeks old) were used as experimental animals. Four animals were housed in each cage. Animals were kept on 20% food deprivation from a day prior to experimentation. Water was provided ad libitum throughout the experiment. Animals were maintained on a 12 hours light/dark cycle in temperature and humidity controlled room. The experiment was carried out in a circular or square arena made up of acrylic. Rats were habituated to individual arenas for up to 1 hour in the absence of any objects on day 1.

One group of 12 rats received vehicle and another set of animals received compound of the formula (I), before the familiar ($T_1$) and choice ($T_2$) trials. During the familiarization phase, ($T_1$), the rats were placed individually in the arena for 3 minutes, in which two identical objects ($a_1$ and $a_2$) were positioned 10 cm from the wall. 24 hours after $T_1$, trial for long-term memory test was performed. The same rats were placed in the same arena as they were placed in $T_1$ trial. During the choice phase ($T_2$) rats were allowed to explore the arena for 3 minutes in presence of a copy of familiar object ($a_3$) and one novel object (b). During the $T_1$ and $T_2$ trial, explorations of each object (defined as sniffing, licking, chewing or having moving vibrissae whilst directing the nose towards the object at a distance of less than 1 cm) were recorded using stopwatch.

$T_1$ is the total time spent exploring the familiar objects ($a_1+a_2$).

$T_2$ is the total time spent exploring the familiar object and novel object ($a_3+b$).

The object recognition test was performed as described by Ennaceur, A., Delacour, J., 1988, A new one-trial test for neurobiological studies of memory in rats~Behavioural data, Behav. Brain Res., 31, 47-59.

| Example No. | Dose | Exploration time mean ± S.E.M (sec) | | Inference |
|---|---|---|---|---|
| | | Familiar object | Novel object | |
| 20 | 1 mg/kg, p.o. | 10.31 ± 1.07 | 14.92 ± 1.11 | Active |
| 32 | 3 mg/kg, p.o. | 11.64 ± 2.16 | 19.81 ± 2.96 | Active |
| 34 | 0.3 mg/kg, p.o. | 10.35 ± 1.75 | 15.63 ± 3.23 | Active |

Example 56

Evaluation of Theta Modulation in Dorsal Hippocampus of Anesthetized Male Wistar Rats in Combination with Acetylcholine Esterase Inhibitor Donepezil Effect of M1 PAM compound (Example 32) in combination with donepezil on brain activity as a pharmacodynamic endpoint is evaluated.

Male Wistar rats (240-320 g) were anesthetized by Intraperitoneal administration of urethane (1.2 to 1.5 g/Cp) for implantation of a catheter in the left femoral vein. The animal was placed in a stereotaxic frame for implanting an electrode (stainless steel wire, Plastics One) into the dorsal hippocampus (AP: −3.8 mm; ML: +2.2 mm; DV: −2.5 mm; Paxinos and Watson, 2004). Bipolar stimulating electrode (untwisted stainless steel wires, separated by 0.75-1.0 mm at their tips, Plastics One) was implanted in the Nucleus Pontis Oralis (NPO; AP: −7.8 mm; ML: 1.8 mm; DV: −6.0 mm; Paxinos and Watson, 2004). Additionally one electrode was implanted into the cerebellum which served as a reference. Hippocampal θ rhythm was evoked via a 6-s electrical stimulation train (20-160 μA, 0.3-ms pulse duration, 250 Hz) delivered to the NPO at a rate of 0.01 trains/s with a Grass S88 stimulator and PSIU6 stimulus isolation unit (Grass Medical Instruments, Quincy, Mass.). EEG was recorded at a rate of 1000 Hz using Ponemah (Version 5.2) software and stored for off-line analysis using NeuroScore (Version 3.0). Baseline amplitude level was achieved by using the current required to elicit θ rhythm to 50% of the maximal amplitude under control conditions. After the stabilization period of one hour, baseline recording was done for 30 min followed by the treatment of vehicle or Example 32 (1 mg/kg, i.v.). Donepezil (0.3 mg/kg, i.v.) was administered 30 min after Example 32 treatment and recording was continued for additional 1 hour.

Statistical Analysis:

Power in the θ rhythm frequency in the stimulation period during the 30-min baseline period was calculated and the % changes in these measures post treatment were calculated. The percent change in relative theta power after combination of Example 32 and donepezil was compared with donepezil using two-way analysis of variance (time and treatment), followed by Bonferroni's posttest. Statistical significance was considered at a p value less than 0.05.

REFERENCE

1. Paxinos G. and Watson C. (2004) Rat brain in stereotaxic coordinates. Academic Press, New York.

Results:

Treatment with donepezil produced moderate increase in hippocampal θ power. Example 32 in combination with donepezil produced significant increase in θ power levels. The effect in combination treatment was observed to be significantly higher than the donepezil alone (The FIGURE). Mean area under the curve values (AUC) calculated after the treatment of Example 32 and donepezil was significantly higher compared to donepezil alone treatment (The FIGURE).

We claim:

1. A compound of formula (I),

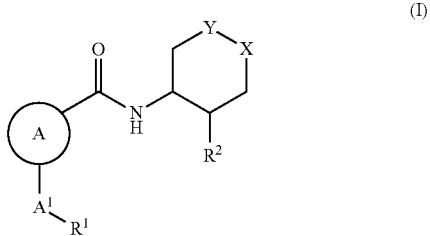

or an isotopic form, a stereoisomer, a tautomer or a pharmaceutically acceptable salt thereof, wherein:

$R^1$ is —$(C_{6-10})$-aryl, —$(C_{6-10})$-heteroaryl or —$(C_{6-10})$-heterocyclyl; each of which is optionally substituted with one or more substituents selected from halogen, —OH, —O—$(C_{1-6})$-alkyl, —S—$(C_{1-6})$-alkyl, —N(CH$_3$)$_2$, —$(C_{1-6})$-alkyl, —$(C_{3-6})$-cycloalkyl, halo$(C_{1-6})$-alkyl, —NH$_2$, —CN and $R^{1a}$;

$R^{1a}$ is —$(C_{6-10})$-aryl or —$(C_{5-10})$-heteroaryl; each of which is optionally substituted with one or more substituents selected from the group consisting of halogen, —OH, —NH$_2$, —CN, —O—$(C_{1-6})$-alkyl, —S—$(C_{1-6})$-alkyl, —$(C_{1-6})$-alkyl and —$(C_{3-6})$-cycloalkyl;

$A^1$ is CH$_2$ or CHF;

$R^2$ is hydrogen or OH;

ring A is

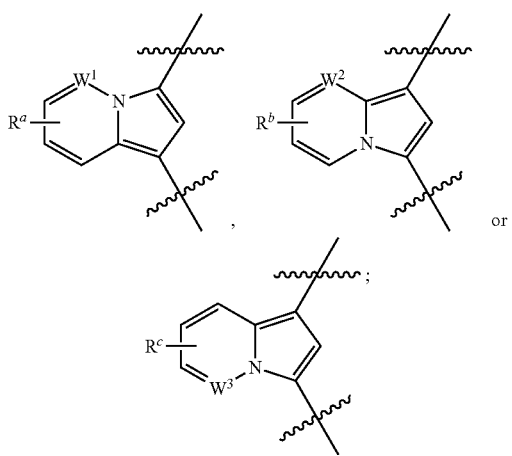

"⁓" represents point of attachment;

$W^1$ is independently represents C—F or N;
$W^2$ is independently represents C—F or N;
$W^3$ is independently represents C—F or N;
$R^a$ is hydrogen, halogen, —OH, —$(C_{1-6})$-alkyl, —O—$(C_{1-6})$-alkyl or halo$(C_{1-6})$-alkyl;
$R^b$ is hydrogen, halogen, —OH, —$(C_{1-6})$-alkyl, —O—$(C_{1-6})$-alkyl or halo$(C_{1-6})$-alkyl;
$R^c$ is hydrogen, halogen, —OH, —$(C_{1-6})$-alkyl, —O—$(C_{1-6})$-alkyl or halo$(C_{1-6})$-alkyl;
X is CH$_2$, O or NH; and
Y is CH$_2$, O or NH.

2. The compound as claimed in claim 1, wherein the compound is selected from the group consisting of:

N-(cis-1S,2S-2-Hydroxycyclohexyl)-5-(4-bromobenzyl)-pyrrolo[1,2-b]pyridazine-7-carboxamide;

N-(cis-1S,2S-2-Hydroxycyclohexyl)-5-(5-bromo-2-fluorobenzyl)-pyrrolo[1,2-b]pyridazine-7-carboxamide;

N-(cis-1S,2S-2-Hydroxycyclohexyl)-5-(4-bromo-3-fluorobenzyl)-pyrrolo[1,2-b]pyridazine-7-carboxamide;

N-(cis-1S,2S-2-Hydroxycyclohexyl)-5-(2,3-dihydrobenzofuran-5-ylmethyl)-pyrrolo[1,2-b]pyridazine-7-carboxamide;

N-(cis-1S,2S-2-Hydroxycyclohexyl)-5-(2-bromo-pyridin-5-ylmethyl)-pyrrolo[1,2-b]pyridazine-7-carboxamide;

N-(cis-1S,2S-2-Hydroxycyclohexyl)-5-(3-methoxybenzyl)-pyrrolo[1,2-b]pyridazine-7-carboxamide;

N-(cis-1S,2S-2-Hydroxycyclohexyl)-5-(2,4-difluorobenzyl)-pyrrolo[1,2-b]pyridazine-7-carboxamide;

N-(cis-1S,2S-2-Hydroxycyclohexyl)-5-(4-fluorobenzyl)-pyrrolo[1,2-b]pyridazine-7-carboxamide;

N-(cis-1S,2S-2-Hydroxycyclohexyl)-5-(2,3-difluorobenzyl)-pyrrolo[1,2-b]pyridazine-7-carboxamide;

N-(cis-1S,2S-2-Hydroxycyclohexyl)-5-(3-fluoro-4-methoxybenzyl)-pyrrolo[1,2-b]pyridazine-7-carboxamide;

N-(cis-1S,2S-2-Hydroxycyclohexyl)-5-(2-chloro-pyridin-4-ylmethyl)-pyrrolo[1,2-b]pyridazine-7-carboxamide;

N-(cis-1S,2S-2-Hydroxycyclohexyl)-5-(4-fluoro-3-methoxybenzyl)-pyrrolo[1,2-b]pyridazine-7-carboxamide;

N-(cis-1S,2S-2-Hydroxycyclohexyl)-5-(2-fluorobenzyl)-pyrrolo[1,2-b]pyridazine-7-carboxamide;

N-(cis-1S,2S-2-Hydroxycyclohexyl)-5-(2-fluoro-4-methoxybenzyl)-pyrrolo[1,2-b]pyridazine-7-carboxamide;

N-(cis-1S,2S-2-Hydroxycyclohexyl)-5-(3,4-difluorobenzyl)-pyrrolo[1,2-b]pyridazine-7-carboxamide;

N-(cis-1S,2S-2-Hydroxycyclohexyl)-5-(2-chloro-pyridin-5-ylmethyl)-pyrrolo[1,2-b]pyridazine-7-carboxamide;

N-(Tetrahydropyran-4-yl)-5-(2-chloropyridin-5-ylmethyl)-pyrrolo[1,2-b]pyridazine-7-carboxamide;

N-(cis-1S,2S-2-Hydroxycyclohexyl)-5-(2-fluoro-3-methoxybenzyl)-pyrrolo[1,2-b]pyridazine-7-carboxamide;

N-(cis-1S,2S-2-Hydroxycyclohexyl)-5-(3-fluorobenzyl)-pyrrolo[1,2-b]pyridazine-7-carboxamide;

N-(cis-1S,2S-2-Hydroxycyclohexyl)-5-(4-methoxybenzyl)-pyrrolo[1,2-b]pyridazine-7-carboxamide;

N-(cis-1S,2S-2-Hydroxycyclohexyl)-5-(4-pyrazol-1-yl-benzyl)-pyrrolo[1,2-b]pyridazine-7-carboxamide;

N-(Tetrahydropyran-4-yl)-5-(4-pyrazol-1-ylbenzyl)-pyrrolo[1,2-b]pyridazine-7-carboxamide;

N-(cis-1S,2S-2-Hydroxycyclohexyl)-5-(4-thiazol-4-yl-benzyl)-pyrrolo[1,2-b]pyridazine-7-carboxamide;

N-(cis-1S,2S-2-Hydroxycyclohexyl)-5-(2-bromo-4-fluorobenzyl)-pyrrolo[1,2-b]pyridazine-7-carboxamide;
N-(cis-1S,2S-2-Hydroxycyclohexyl)-5-(2,3-difluoro-4-bromobenzyl)-pyrrolo[1,2-b]pyridazine-7-carboxamide;
N-(cis-1S,2S-2-Hydroxycyclohexyl)-5-(3-bromo-4-fluorobenzyl)-pyrrolo[1,2-b]pyridazine-7-carboxamide;
N-(cis-1S,2S-2-Hydroxycyclohexyl)-5-(3-bromobenzyl)-pyrrolo[1,2-b]pyridazine-7-carboxamide;
N-(cis-1S,2S-2-Hydroxycyclohexyl)-5-(2-chloropyridin-3-ylmethyl)-pyrrolo[1,2-b]pyridazine-7-carboxamide;
N-(cis-1S,2S-2-Hydroxycyclohexyl)-5-(2-bromopyridin-4-ylmethyl)-pyrrolo[1,2-b]pyridazine-7-carboxamide;
N-(3-Hydroxytetrahydropyran-4-yl)-5-(3-fluorobenzyl)-pyrrolo[1,2-b]pyridazine-7-carboxamide;
N-(3-Hydroxytetrahydropyran-4-yl)-5-(4-bromobenzyl)-pyrrolo[1,2-b]pyridazine-7-carboxamide;
N-(cis-1S,2S-2-Hydroxycyclohexyl)-5-[4-(1-methyl-1H-pyrazol-4-yl)-benzyl]-pyrrolo[1,2-b]pyridazine-7-carboxamide;
N-(cis-1S,2S-2-Hydroxycyclohexyl)-5-[3-fluoro-4-(1-methyl-1H-pyrazol-4-yl)-benzyl]-pyrrolo[1,2-b]pyridazine-7-carboxamide;
N-(cis-1S,2S-2-Hydroxycyclohexyl)-5-[2-fluoro-4-(1-methyl-1H-pyrazol-4-yl)-benzyl]-pyrrolo[1,2-b]pyridazine-7-carboxamide;
N-(cis-1S,2S-2-Hydroxycyclohexyl)-5-[6-(1-methyl-1H-pyrazol-4-yl)-pyridin-3-ylmethyl]-pyrrolo[1,2-b]pyridazine-7-carboxamide;
N-(cis-1S,2S-2-Hydroxycyclohexyl)-5-[2,3-difluoro-4-(1-methyl-1H-pyrazol-4-yl)-benzyl]-pyrrolo[1,2-b]pyridazine-7-carboxamide;
N-(cis-1S,2S-2-Hydroxycyclohexyl)-5-[4-fluoro-3-(1-methyl-1H-pyrazol-4-yl)-benzyl]-pyrrolo[1,2-b]pyridazine-7-carboxamide;
N-(cis-1S,2S-2-Hydroxycyclohexyl)-5-[3-(1-methyl-1H-pyrazol-4-yl)-benzyl]-pyrrolo[1,2-b]pyridazine-7-carboxamide;
N-(3-Hydroxytetrahydropyran-4-yl)-5-[4-(1-methyl-1H-pyrazol-4-yl)-benzyl]-pyrrolo[1,2-b]pyridazine-7-carboxamide;
N-(cis-1S,2S-2-Hydroxycyclohexyl)-5-[2-(1-methyl-1H-pyrazol-4-yl)-pyridin-4-ylmethyl]-pyrrolo[1,2-b]pyridazine-7-carboxamide;
N-(cis-1S,2S-2-Hydroxycyclohexyl)-3-(4-bromobenzyl)-8-fluoroindolizine-1-carboxamide;
N-(cis-1S,2S-2-Hydroxycyclohexyl)-3-benzyl-8-fluoroindolizine-1-carboxamide;
N-(cis-1S,2S-2-Hydroxycyclohexyl)-3-(2-chloropyridine-4-ylmethyl)-8-fluoroindolizine-1-carboxamide;
N-(cis-1S,2S-2-Hydroxycyclohexyl)-3-(4-methoxybenzyl)-8-fluoroindolizine-1-carboxamide;
N-(cis-1S,2S-2-Hydroxycyclohexyl)-3-(4-thiazol-4-yl-benzyl)-8-fluoroindolizine-1-carboxamide;
N-(3-Hydroxytetrahydropyran-4-yl)-3-(2-chloropyridine-4-ylmethyl)-8-fluoroindolizine-1-carboxamide;
N-(3-Hydroxytetrahydropyran-4-yl)-3-(4-methoxybenzyl)-8-fluoroindolizine-1-carboxamide;
N-(cis-1S,2S-2-Hydroxycyclohexyl)-5-[4-(1-methyl-1H-pyrazol-4-yl)-benzyl]-8-fluoroindolizine-1-carboxamide;
N-(3-Hydroxytetrahydropyran-4-yl)-3-(4-(1-methyl-1H-pyrazol-4-yl)-benzyl)-8-fluoroindolizine-1-carboxamide;
N-(Tetrahydropyran-4-yl)-3-(4-(1-methyl-1H-pyrazol-4-yl)-benzyl)-8-fluoroindolizine-1-carboxamide; and
N-(4-Hydroxytetrahydropyran-3-yl)-3-(4-(1-methyl-1H-pyrazol-4-yl)-benzyl)-8-fluoroindolizine-1-carboxamide;
or a pharmaceutically acceptable salt thereof.

3. A pharmaceutical composition comprising the compound of formula (1) or a pharmaceutically acceptable salt thereof as claimed in claim 1 and pharmaceutically acceptable excipients.

4. The pharmaceutical composition as claimed in claim 3, for the treatment of disease or disorder mediated by muscarinic M1 receptor, wherein said disease or disorder is selected from the group consisting of cognitive disorders, Alzheimer's disease, schizophrenia, pain or sleep disorder.

5. A method of treatment of disease or disorder mediated by muscarinic M1 receptor, wherein the disease or disorder is selected from the group consisting of cognitive disorders, Alzheimer's disease, schizophrenia, pain or sleep disorder comprising administering to a patient in need thereof, a therapeutically effective amount of the compound of formula (I) or a pharmaceutically acceptable salt thereof as claimed in claim 1.

6. The method of treating disease or disorder as claimed in claim 5, wherein the cognitive disorder is selected from the group consisting of dementia in Alzheimer's disease, dementia in Parkinson's disease, dementia in Huntington's disease, dementia associated with Down syndrome, dementia associated with Tourette's syndrome, dementia associated with post menopause, frontotemporal dementia, Lewy body dementia, Vascular dementia, dementia in HIV, dementia in Creutzfeldt-Jakob disease, substance-induced persisting dementia, dementia in Pick's disease, dementia in schizophrenia, senile dementia and dementia in general medical conditions.

7. A combination comprising the compound as claimed in claim 1 with one or more therapeutic agents selected from acetylcholinesterase inhibitors and NMDA receptor antagonist.

8. The combination as claimed in claim 7, wherein the acetylcholinesterase inhibitor is selected from the group consisting of donepezil, rivastigmine, tacrine and galantamine or a pharmaceutically acceptable salt thereof.

9. The combination as claimed in claim 7, wherein the NMDA receptor antagonist is memantine or a pharmaceutically acceptable salt thereof.

10. The combination as claimed in claim 7, for the treatment of cognitive disorders, Alzheimer's disease, schizophrenia, pain or sleep disorder.

11. A combination comprising the compound as claimed in the claim 2 with one or more therapeutic agents selected from acetylcholinesterase inhibitors and NMDA receptor antagonist.

12. The combination as claimed in claim 11, wherein the acetylcholinesterase inhibitor is selected from the group consisting of donepezil, rivastigmine, tacrine and galantamine or a pharmaceutically acceptable salt thereof.

13. The combination as claimed in claim 11, wherein the NMDA receptor antagonist is memantine or a pharmaceutically acceptable salt thereof.

14. The combination as claimed in claim 11, for the treatment of cognitive disorders, Alzheimer's disease, schizophrenia, pain or sleep disorder.

15. A pharmaceutical composition comprising the compound of formula (I) or a pharmaceutically acceptable salt thereof as claimed in the claim 2 and pharmaceutically acceptable excipients.

16. The pharmaceutical composition as claimed in claim 15, for the treatment of disease or disorder mediated by muscarinic M1 receptor, wherein said disease or disorder is selected from the group consisting of cognitive disorders, Alzheimer's disease, schizophrenia, pain or sleep disorder.

17. A method of treatment of disease or disorder mediated by muscarinic M1 receptor, wherein the disease or disorder is selected from the group consisting of cognitive disorders, Alzheimer's disease, schizophrenia, pain or sleep disorder comprising administering to a patient in need thereof, a therapeutically effective amount of the compound of formula (I) or a pharmaceutically acceptable salt thereof as claimed in the claim 2.

18. The method of treating disease or disorder as claimed in claim 17, wherein the cognitive disorder is selected from the group consisting of dementia in Alzheimer's disease, dementia in Parkinson's disease, dementia in Huntington's disease, dementia associated with Down syndrome, dementia associated with Tourette's syndrome, dementia associated with post menopause, frontotemporal dementia, Lewy body dementia, Vascular dementia, dementia in HIV, dementia in Creutzfeldt-Jakob disease, substance-induced persisting dementia, dementia in Pick's disease, dementia in schizophrenia, senile dementia and dementia in general medical conditions.

* * * * *